(12) United States Patent
Nutley et al.

(10) Patent No.: US 8,396,667 B2
(45) Date of Patent: Mar. 12, 2013

(54) METHOD AND APPARATUS FOR TESTING SWELLABLE MATERIALS

(75) Inventors: Kim Nutley, Iverurie (GB); Brian Nutley, Aberdeen (GB)

(73) Assignee: Swelltec Limited, Dyce, Aberdeen (GB)

( * ) Notice: Subject to any disclaimer, the term of this patent is extended or adjusted under 35 U.S.C. 154(b) by 402 days.

(21) Appl. No.: 12/607,452

(22) Filed: Oct. 28, 2009

(65) Prior Publication Data

US 2010/0138158 A1    Jun. 3, 2010

(30) Foreign Application Priority Data

Oct. 28, 2008 (GB) .................................. 0819749.3

(51) Int. Cl.
G06F 19/00 (2011.01)
G01N 33/00 (2006.01)
E21B 47/00 (2012.01)

(52) U.S. Cl. .......................... 702/6; 73/866; 166/250.01

(58) Field of Classification Search .............. 702/6, 108; 73/152.24, 866, 855.6, 61.41, 152.18; 166/250.01
See application file for complete search history.

(56) References Cited

U.S. PATENT DOCUMENTS

| 5,503,013 | A  | * | 4/1996  | Zeller ........................ 73/152.18 |
| 5,587,525 | A  | * | 12/1996 | Shwe et al. ................ 73/152.52 |
| 7,866,408 | B2 | * | 1/2011  | Allison et al. ................ 166/387 |
| 2004/0014226 | A1 |  | 1/2004  | Schrof et al. |

FOREIGN PATENT DOCUMENTS

| DE | 222960  | 5/1985 |
| EP | 0104153 | 3/1984 |
| GB | 2235300 | 2/1991 |
| GB | 2411918 | 9/2005 |
| GB | 2448099 | 10/2008 |

OTHER PUBLICATIONS

Great Britain Search Report and Search Opinion for GB Application No. 0918889.7, dated Feb. 24, 2010, 6 pages.

* cited by examiner

*Primary Examiner* — Bryan Bui
(74) *Attorney, Agent, or Firm* — Wong, Cabello, Lutsch, Rutherford & Brucculeri, LLP

(57) ABSTRACT

The invention provides a method and apparatus for use in testing the swell characteristics of swellable components used in downhole exploration or production equipment, such as swellable packers. A method of measuring a test piece using a testing apparatus with a fluid chamber and a transducer is described. Measured data can be compared with data measured from a sample section of a tool to determine a relationship between swell characteristics. The determined relationships can then be used to calculate or predict swelling characteristics of swellable components, for example particular packer designs, in specific fluid samples.

77 Claims, 16 Drawing Sheets

METHOD AND APPARATUS FOR TESTING SWELLABLE MATERIALS

CROSS-REFERENCE TO RELATED APPLICATIONS

This application claims priority United Kingdom Patent Application No. GB0819749.3, filed on Oct. 28, 2008, which is hereby incorporated by reference in its entirety.

FIELD OF THE INVENTION

The present invention relates to a method and apparatus for testing of swellable materials and in particular to a method and apparatus for testing of swell characteristics of materials and components used in downhole equipment for the oil and gas exploration and production industries.

BACKGROUND

Swellable materials have been used in a range of oil and gas exploration and production equipment. Most notably, swellable materials have been used in wellbore packers for creating a seal in an annular space between a tubing and a surrounding wall of a cased hole or openhole well. A typical swellable packer includes a mantle of swellable elastomeric material formed around a tubular body. The swellable elastomer is selected to increase in volume on exposure to at least one triggering fluid, which may be hydrocarbon fluid or an aqueous fluid or brine. The packer is run to a downhole location in its unexpanded, unswollen state where it is exposed to a wellbore fluid and caused to swell. The design, dimensions, and swelling characteristics are selected such that the swellable mantle creates a fluid seal in the annulus, thereby isolating one wellbore section from another. Swellable packers have several advantages over conventional packers, including passive actuation, simplicity of construction, and robustness in long term isolation applications. Examples of swellable packers and suitable materials are described in GB 2411918.

The swell characteristics of the packer are critical to proper performance of the packer. Important swell characteristics include the swell rate, the time taken for the outer surface of the mantle to reach and contact the exterior surface (which may be referred to generally as "contact time") and the time taken to reach the point of maximum internal pressure exerted by the packer on the surrounding surface (which may be referred to generally as "pack-off time"). The swell characteristics are dependent on various factors including the materials used, the dimensions and design of the tool, the wellbore conditions (including temperature and pressure), and the fluid or fluids to which the tool is exposed.

It is known in the art to carry out tests on swellable packers by placing a representative sample of the packer in a fluid. A typical sample packer section is shown in FIG. 1, generally depicted at 10. A swellable mantle 12 is formed on a pipe or mandrel 14 according to conventional manufacturing techniques and has a known outer diameter and thus a known mantle thickness. The packer section 10 is formed by cutting a short length, for example 8 to 15 cm, through the mantle 12 and the pipe 14. The sample packer section 10 is placed in a fluid bath (not shown), which contains a hydrocarbon or aqueous fluid or brine used for the test. The fluid bath is located inside an oven, which can be heated to typical wellbore temperatures. For example, the oven may be operable to heat the fluid and packer section 10 to temperature of around 80° C. to 150° C. The packer section 10 is left in the fluid bath for the duration of the test (which may be several days). At regular intervals during the test, the oven is opened, the packer section is removed, and the outer diameter is measured manually using a calliper gauge. The measurement data for such packer sections 10 are generally considered by the industry to be representative of the swell times of a complete tool of the same radial dimensions and configuration in a wellbore environment.

FIG. 2 is a plot of thickness change, expressed as a percentage of the original thickness, versus exposure time of a sample packer section 10 with an initial outer diameter of 5.75 inches (approximately 146 mm) on a base pipe having outer diameter of 4.5 inches (around 114 mm). The packer section 10 of this example had a swellable mantle 12 formed from ethylene propylene diene M-class rubber (EPDM) rubber and was exposed to Clairsol® (a hydrocarbon fluid) at 90° C. The data show that the time taken for the sample section to swell to its maximum volume (with a percentage thickness increase of around 80%) is around 600 hours or 25 days.

A packer will be deployed in and sealing with a wellbore of known inner diameter. For example, the packer 10 for the test data of FIG. 2 is designed for sealing with a bore of inner diameter in the range of 6 to 6.8 inches (about 152.4 mm to 172.7 mm). The measurements of particular interest are the time taken for a swellable mantle to increase in outer diameter to contact a surrounding surface of a wellbore of a particular inner diameter (the "contact time") and the time taken for the swellable mantle to exert its maximum internal pressure against a sealing surface of a particular inner diameter (the "pack-off time"). In the example of FIG. 2, the packer has a contact time of 60 hours with a 6.125 inch (about 155.6 mm) wellbore.

Performing such tests on packer sections requires an oven and a suitable fluid chamber, which typically lacks portability and takes up valuable space at an exploration or production installation. Carrying out the tests is labour intensive, and may be hazardous due to the nature of the fluids used and the elevated temperatures. Physical handling of the sample sections may be difficult or unsafe when the packer sections have been exposed to fluid, particularly at high temperatures. Measurement of the outer diameter is prone to error, particularly because the swellable material is soft and may be deformed by the callipers. Multiple personnel may be required to measure the outer diameter at different measurement times, and each individual may take a measurement by a slightly different technique, introducing further uncertainty into the measurement data. The long swelling times of the sample packer sections are inconvenient for rapid measurement of swell characteristics. The long test times also increase the likelihood of multiple personnel being used to measure the outer diameter, and therefore increase the likelihood of inconsistent measurements. Long test times limit the repeatability of the tests, and reduce the practicability of tests being carried out for multiple fluid samples. These factors combine to reduce the quality of the available measurement data.

With packer sample section 10 of the prior art, the ends of the swellable member 12 are exposed to the test fluid, which increases the surface area-to-volume ratio at each end of the section 10, relative to the surface area-to-volume ratio at its axial midpoint. This means that the swelling rate of the swellable member at the end of the sample section 10 is likely to be greater than the swelling rate at its axial midpoint, causing non-uniform swelling which can have an adverse effect on the accuracy of the measurements of the outer diameter.

The industry tends to make assumptions about the swell characteristics of swellable materials in different fluids. For example, a simplified model of volume increase of swellable elastomers assumes that the swell rate of a swellable material depends primarily on the viscosity of the fluid to which it has exposed. Accordingly, a sample packer section 10 may be tested in a fluid of low viscosity (for example 1 cP), with measurements of percentage change in thickness over time being made. Measurements may also be made for an identical sample packer section in a higher viscosity of fluid (for example 100 cP or 100 mPa). In order to predict the swell characteristics of a packer section in a given wellbore fluid sample with a different viscosity, the measurement data will be interpolated or extrapolated rather than repeating the tests in the wellbore fluid sample.

Additionally, in some simplified models, the pack-off time for a particular inner diameter is assumed to be constant multiplier of the contact time. This simplified model is flawed, because it does not account for different swelling end points of a swellable material in different fluid samples. For example, a packer sample section exposed to one hydrocarbon fluid with 1 cP viscosity might have a maximum swelling extent of, for example 75% of the original mantle thickness, whereas the swelling end point of an identical tool sample in a different hydrocarbon fluid, also having a viscosity of 1 cP, may have a swelling end point of 80% of the original thickness of the mantle. FIG.3 is a plot of swelling profile of two identical sample sections in different hydrocarbon-based fluids with the same viscosity (1.5 cP). The plot shows that the swell characteristics of the sample in Fluid 1 (which was the special kerosine Clairsol 350 MHF™) are different from the swell characteristics of the sample in Fluid 2 (which was a gas oil) despite the test fluids having the same fluid viscosity. Different swelling end points have an effect on the contact time and pack-off time, which is not accounted for in a model which relies on viscosity effects only. This illustrates that it would be advantageous to account for fluid types when assessing swell characteristics.

It is amongst the aims and the objects of the invention to provide methods, testing apparatus, and test pieces which overcome or mitigate the drawbacks of conventional testing procedures and apparatus.

Further aims and objects of the invention will become apparent from the following description.

SUMMARY OF THE INVENTION

According to a first aspect of the invention, there is provided a method of testing a swellable component for downhole hydrocarbon exploration or production equipment, the method comprising the steps of: providing a test piece comprising a swellable material in a fluid chamber of a testing apparatus; exposing the test piece to a triggering fluid; measuring, using a transducer of the testing apparatus, a swell characteristic of the test piece to provide a test piece measurement data set.

The test piece may be a small, portable test piece which is easy to handle and which can be tested in a small, portable test apparatus. The swell characteristics measured may for example be thickness of the test piece (or another dimension) or a pressure exerted by the test piece during swelling.

The method may comprise the additional step of outputting the measurement data set to a data processing means. The data processing means may be a personal computer, or alternatively maybe a dedicated data processing module.

The method may comprise generating a report of the swell characteristic. Preferably, the measurement data set comprises a time series of a swell characteristic, and the method comprises generating a report of the measurement data set as a changing swell characteristic or parameter over time.

The fluid may comprise a hydrocarbon fluid. Alternatively, or in addition, the fluid may comprise an aqueous fluid or brine. The fluid may be a sample of a fluid to which downhole equipment will be exposed in a wellbore. Thus, when testing a swellable material for use in downhole equipment for a particular wellbore installation, a sample of wellbore fluid used in that installation may be used in the method to measure a swell characteristic of the sample in that fluid. The fluid may be a drilling mud, a completion fluid, or a production fluid. Other fluids are within the scope of the invention.

The method may comprise the step of exposing the sample to a second fluid or to a second fluid mixture. Thus the sample may be exposed to a first fluid for a period of time, with swell characteristics measured during that period. The sample may be exposed to a second fluid, different from the first, for a second period of time in order to measure the swell characteristic of the sample when exposed to the second fluid.

The method may comprise the additional step of circulating fluid in the chamber. Thus, according to one embodiment, the sample may be exposed to a first fluid for a period of time, following which the first fluid may be circulated out of a chamber and replaced by a second fluid. After a further period, the first fluid may be circulated in the chamber to replace the second fluid. Alternatively, a third fluid may replace the second fluid. According to this embodiment, the method may simulate the exposure of the sample to different fluids, as might occur during deployment of downhole equipment, or during the operational lifetime of the downhole equipment. For example, the method may be used to monitor the effect of circulating a completion fluid such as a brine, past the equipment, before being exposed to hydrocarbon fluid such as a drilling fluid or produced hydrocarbons. The method allows a swell characteristic to be measured throughout exposure to different fluid types.

The method may comprise the step of heating and/or cooling the chamber of the apparatus. The method may therefore simulate wellbore conditions, and in particular may expose the sample to an environment similar to that found in a downhole wellbore installation. In particular the method may comprise the step of increasing the temperature of the test piece. Thus the method may simulate an increasing temperature experienced by downhole equipment during run-in. The method may comprise the step of introducing a sharp temperature change to the chamber. This may simulate the injection of a fluid passed the swellable apparatus, the fluid being at a different temperature from the ambient conditions in the wellbore. Such conditions may for example occur during a wellbore clean-up operation.

Changing the temperature profile of the chamber may comprise the step of circulating a fluid in the chamber at a different temperature. The method may include the step of heating or cooling the sample or fluid by a joule heater or Peltier device.

The method may comprise the additional step of determining a relationship between a swell characteristic of the test piece and a swell characteristic of a downhole tool. The relationship may in particular be a time domain scaling between the respective time series. The method also may comprise calculating swelling data for a swellable component of hydrocarbon exploration or production equipment from the test piece measurement data, using a determined relationship between a test piece swell characteristic and a swellable component swell characteristic.

The method may comprise providing swellable component configuration data, and storing the swellable component configuration data in a database with the determined relationship.

The swellable component configuration data is data about the component, and may for example include at least one of: dimensions of the swellable component; shape of the swellable component; materials used in the swellable component; and construction techniques used to form the swellable component. Therefore a determined relationship can be assigned to or identified with a particular swellable component.

The method may comprise deriving a ratio of a dimension of the swellable component to a dimension of the test piece from the swellable component configuration data. For example a ratio of the thickness of a swellable component to the thickness of the swellable material in the test piece may be derived from the swellable component configuration data.

The method may comprise the steps of: a. providing an additional measurement data set comprising measurement data corresponding to an additional swellable component swell characteristic; b. comparing the first and additional measurement data sets to determine an additional relationship between a test piece swell characteristic and the additional swellable component swell characteristic.

Therefore for a single test of a test piece, relationships can be determined with swellable components of different configurations and stored in a database.

The method as claimed may comprise repeating steps a. and b. for at least one further swellable component, and storing the plurality of determined relationships in a database with the swellable component configuration data.

For example, in the context of swellable packers, relationships with swelling profiles of packers of different sizes can be calculated. This can be repeated, with the relationships stored in the database.

The method may also comprise deriving a further relationship between the swellable component configuration data and the plurality of determined relationships. For example, a further relationship between the ratio of the thickness of a swellable component to the thickness of the swellable material in the test piece, and the time domain scaling multiplier can be determined. This allows prediction of swell characteristics of a tool configuration, even where a specific tool configuration has not been tested.

According to a second aspect of the invention there is provide an apparatus for testing a swell characteristic of a material used in a swellable component of downhole hydrocarbon exploration or production equipment, the apparatus comprising: a fluid chamber configured to receive a fluid and a test piece comprising a swellable material; and a transducer for measuring a swell characteristic of the test piece.

The apparatus may comprise an output line for outputting measurement data from the transducer, which may be operable to measure a dimension of the test piece, such as a thickness. The transducer may be a non-contact transducer which tracks movement of a target coupled to the test piece. In one embodiment, the transducer is an eddy current transducer and is disposed to measure an eddy current in the target. The target may be configured to move in correspondence with an increase in volume of the swellable material of the test piece. Alternatively, the transducer may be a contact transducer.

A movable plate may be provided which may be provided, and may be configured for movement in a single direction (which is preferably vertical). The movable plate moves in correspondence to an increase in volume of the swellable material of the test piece. Wherein the transducer is a contact transducer, the movable member is disposed to contact the head of the transducer. The movable member may impart a force or pressure on to the transducer The apparatus may include a temperature control system, which may have a heating element operable to heat fluid in the fluid chamber and may comprise a temperature feedback loop. The apparatus may comprise an inlet and/or an outlet for the chamber, and may be configured for the circulation of fluid in the fluid chamber via the inlet and outlet.

The apparatus may be part of a system of portable components, which may comprise one or more of a data logging unit, a power supply unit, and/or an interface for a portable computer.

According to a third aspect of the invention there is provided method of analysing data obtained from a test of a swellable component of downhole hydrocarbon exploration or production equipment, the method comprising the steps of: providing a first measurement data set comprising measurement data corresponding to a test piece swell characteristic; providing a second measurement data set comprising measurement data corresponding to a swellable component swell characteristic; comparing the first and second measurement data sets to determine a relationship between a test piece swell characteristic and a swellable component swell characteristic.

The first measurement data set may comprise data corresponding to a thickness of the test piece, and the second measurement data set may comprise data corresponding to a dimension of the swellable component. The second measurement data set may for example be data corresponding to an outer diameter of the swellable component (which may be a swellable wellbore packer).

The second measurement data set may be measured from a swellable component sample, such as a packer section sample or a model of a tool, or may be from a full scale tool test.

Preferably the data sets are time series, which may be compared to derive a time domain scaling multiplier for the time values of one of the time series. Thus the relationship between the respective swell characteristics may be a time scaling factor. Thus where the swellable component is a packer, the test piece may comprise a thin piece of swellable material which swells faster than a full size packer. The time domain multiplier may be applied to the time values for the test piece to provide a swell profile which matches that of the packer.

In one embodiment, a plurality of determined relationships is obtained for different swellable components or tool designs, and the determined relationships may have correlation with parameters or features of the swellable components. For example, a relationship may be determined between the time-domain scaling multiplier and the ratio of thickness of the swellable material of the test piece and the thickness of a mantle of a swellable packer. This allows prediction or calculation of a relationship for a tool design from the measured data, which in turn can be used to predict the swelling characteristics of a tool, even when the tool design itself has not been tested. A database may be built up from the determined relationships.

According to a fourth aspect of the invention, there is provided a method of calculating swelling data for a swellable component of downhole hydrocarbon exploration or production equipment, the method comprising the steps of: providing a test piece measurement data set, obtained by disposing a test piece comprising a swellable material in a fluid chamber of a testing apparatus, exposing the test piece to a fluid, and measuring a test piece swell characteristic; calculating swelling data for the swellable component from the test piece measurement data set, using a relationship between a test piece swell characteristic and a swellable component swell characteristic.

The method may comprise obtaining the test piece measurement data set by performing a test on the test piece, or the steps of obtaining the data may be performed separately (at another location) with the data later used in the method of this aspect of the invention.

A wellbore operation may be simulated, for example by altering one or more of the fluid composition, the fluid volume, the fluid temperature, or the test piece temperature during the test. The fluid may be selected to correspond to a fluid to which the swellable component will be exposed during a downhole operation, and may be an actual sample of wellbore fluid to which the swellable component will be exposed during a wellbore operation.

The suitability of the swellable component for a downhole operation may be assessed, based on the calculated swelling data. The method may be repeated to calculate swelling data for a plurality of different swellable components using relationships between a test piece swell characteristic and the respective swellable component characteristics.

Where the swellable component is a part of a wellbore packer, one or more of the following parameters may be calculated to assess the performance and/or suitability of the packer for a particular operation: a time at which the packer will contact a borehole wall of known dimensions; a time at which the packer will exert its maximum pressure against a borehole wall; or a pressure differential rating for the packer in a borehole of known dimensions.

According to a fifth aspect of the invention, there is provided a method of forming a test piece for a swellable component for downhole exploration or production equipment, the method comprising: providing a substantially planar substrate of a non-swellable material; bonding a layer of swellable material selected to increase in volume on exposure at least one triggering fluid onto the substrate.

Preferably, the test piece is substantially planar. The substrate may be metal, and most preferably is steel. The substrate may be a disc of metallic material, having a recess formed in one face of the disc. The swellable material may be moulded into the recess of the disc.

The swellable material may be bonded to the substrate on the base of the recess, and may also be bonded on the side walls of the recess.

The disc may have a thickness in the range of 1 mm to 5 mm. The recess may have a depth in the range of 0.5 mm to 4 mm. The recess preferably has a depth of approximately 2 mm. The swellable material may have a thickness corresponding to the depth of the recess. The thickness is selected to provide portability, along with a rapid swelling rate, balanced with reasonably long overall swelling time to allow sufficient data to be gathered.

According to a sixth aspect of the invention, there is provided a test piece for use in a method of testing a swelling characteristic of a swellable component for downhole exploration or production equipment, the test piece comprising a planar substrate having a recess, and a swellable material selected to increase in volume on exposure at least one triggering fluid moulded into the recess.

According to a seventh aspect of the invention, there is provided a packer section for testing a swelling characteristic of a swellable wellbore packer in a controlled environment, the packer section comprising: a substantially cylindrical body portion having an outer surface; at least one annular recess defined on the body; and a swellable material disposed in the annular recess, the swellable material selected to increase in volume on exposure to at least one triggering fluid; wherein the outer diameter of the outer surface corresponds to the outer diameter of an end ring on the wellbore packer, and the outer diameter defined by a base of the recess corresponds to the outer diameter of a base pipe of the wellbore packer, such that the swellable material defines a swellable body which corresponds to the radial dimensions of a swellable mantle of the wellbore packer.

Preferably, the swellable material is bonded to the body portion at the surface defining the base of the annular recess. The swellable material may alternatively or in addition be bonded to the body portion at the radially extending side walls which define the annular recess.

The annular recess may be formed in the body portion by a machining process. Alternatively, or in addition, the annular recess may be at least partially defined by a ring upstanding from a cylindrical base member or mandrel of the body portion. The ring may be slipped on to the cylindrical base member, or alternatively may be threaded on to the cylindrical base member.

The swellable material may substantially fill the annular recess such that the outer surface of the swellable body is flush with the outer cylindrical surface of the body portion.

The packer model may comprise a plurality of annular recesses. The annular recesses may be formed to different depths.

The swellable material may be selected to increase in volume on exposure to a hydrocarbon triggering fluid, an aqueous triggering fluid, or may be a hybrid swellable material which increases in volume on exposure to either of a hydrocarbon or aqueous triggering fluid. The swellable material may comprise an ethylene propylene diene monomer rubber (EPDM).

Embodiments of the different aspects of the invention may comprise optional or preferred features of any of the other preferred aspect of the invention.

DETAILED DESCRIPTION

Figure 4A:
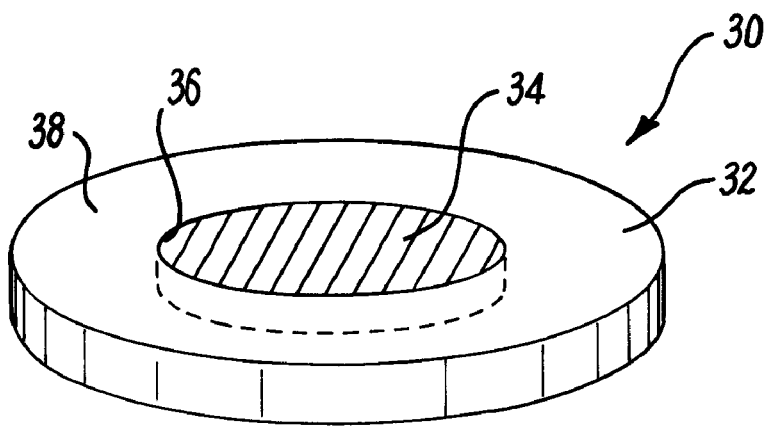
FIGS. 4A and 4B are respectively perspective and sectional views of a test piece in accordance with an embodiment of the invention.
Figure 4B:
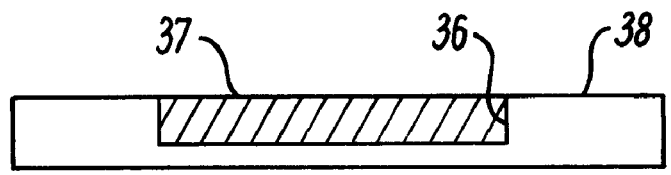

Referring to FIGS. 4A and 4B, there is shown a test piece, generally depicted at 30, in the form of a planar coupon. The test piece 30 facilitates improved methods of testing swell characteristics, and may be used with apparatus according to embodiments of the invention. The test piece 30 comprises a substrate 32 which acts as a carrier and support for a swellable material 34. The substrate 32 is in the form of a planar disc, having a thickness of approximately 0.12 inches (3.05 mm). The disc is formed from a suitable metal, such as carbon steel. A circular recess 36 is formed in a face 38 of the disc to a depth of approximately 0.085 inches (2.16 mm). The recess 36 is filled with a swellable material 34, which may be any material used in swellable components of oilfield equipment which are designed to increase in volume on exposure to a triggering fluid. In this example, the swellable material is ethylene propylene diene M-class (EPDM) rubber, typically used for forming the swellable mantle in a downhole packer. EPDM rubber increases in volume on exposure to a hydrocarbon fluid, such as produced oil. Other materials which are known to swell in hydrocarbon or aqueous fluids or brines are known in the art and are within the scope of the invention.

Figure 5:
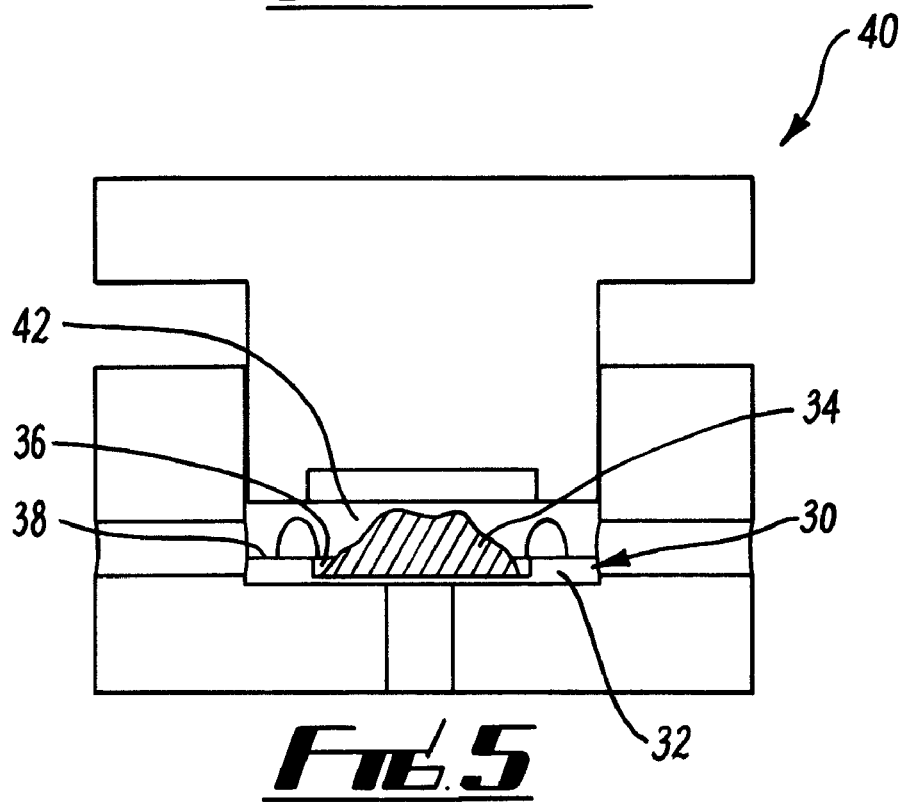
FIG. 5 is a sectional view of a mould used to form the test piece of FIG. 4 in accordance with an embodiment of the invention.

The substrate 32 is machined, and the test piece 30 is completed in a moulding process. FIG. 5 shows schematically a section through a mould, generally depicted at 40, used to form the test piece 30. The substrate 32 is placed inside a chamber 42 in the mould 40. A bonding agent is applied to the lower surface and side walls of the recess 36, and the uncured swellable material is injected into the recess 36. The mould 40 is assembled and pressure will be applied to the upper surface of the swellable material 34 in order to ensure bonding to the substrate and to form the test piece 30 into the desired shape. Depending on the properties of the swellable material used, heat may be applied to cure the swellable material. The resulting test piece 30 may be finished, for example by machining, to provide an upper surface 37 of the swellable material which is flush with the face 38 of the substrate 32. The test piece is bonded to the substrate on its lower surface and its sides, with one unbonded surface 37. This is comparable to the swellable member of a wellbore packer which will typically bonded to a base pipe on its lower surface and to gauge rings or end rings at the radially extending surfaces at its opposing ends.

Figure 1:
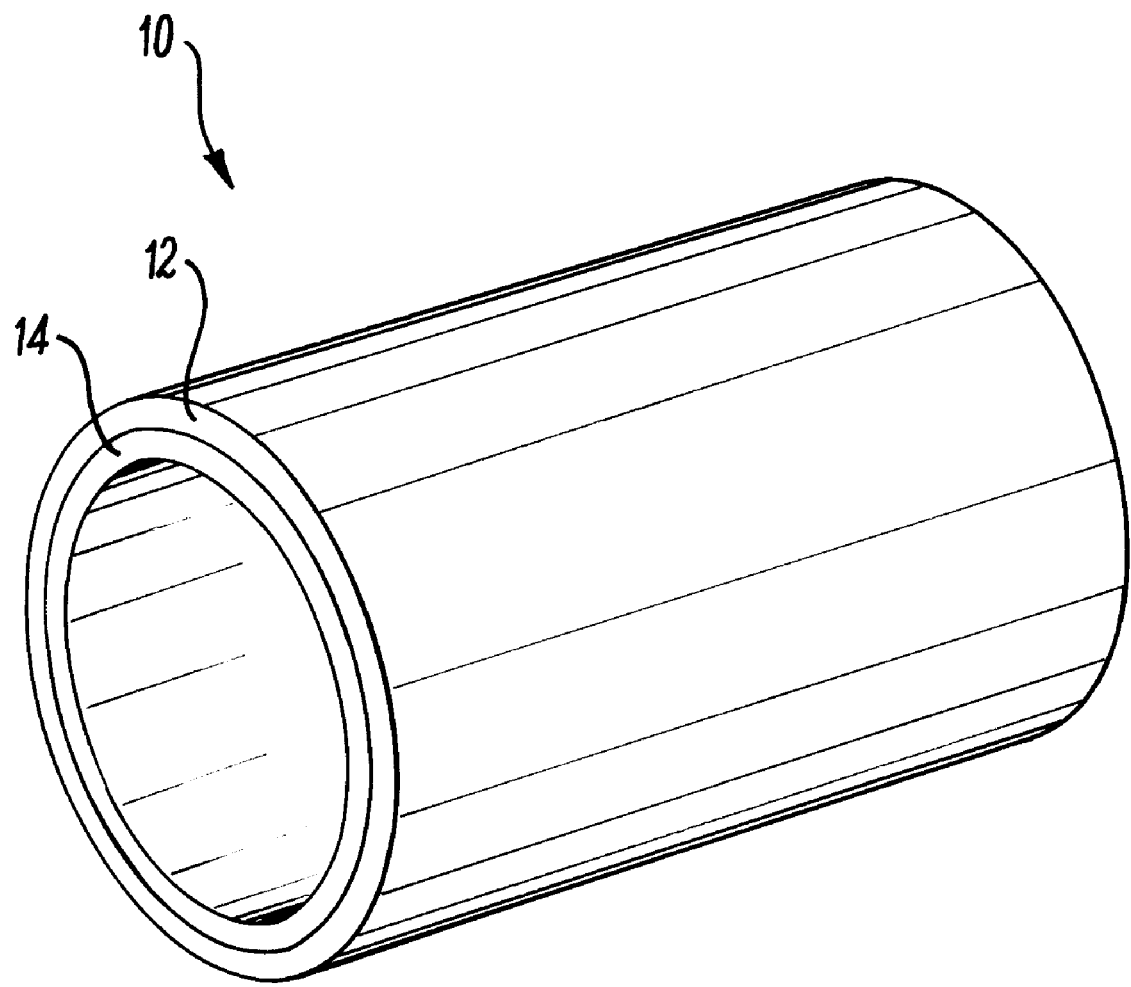
FIG. 1 is a perspective view of a sample section of a swellable packer.
Figure 2:
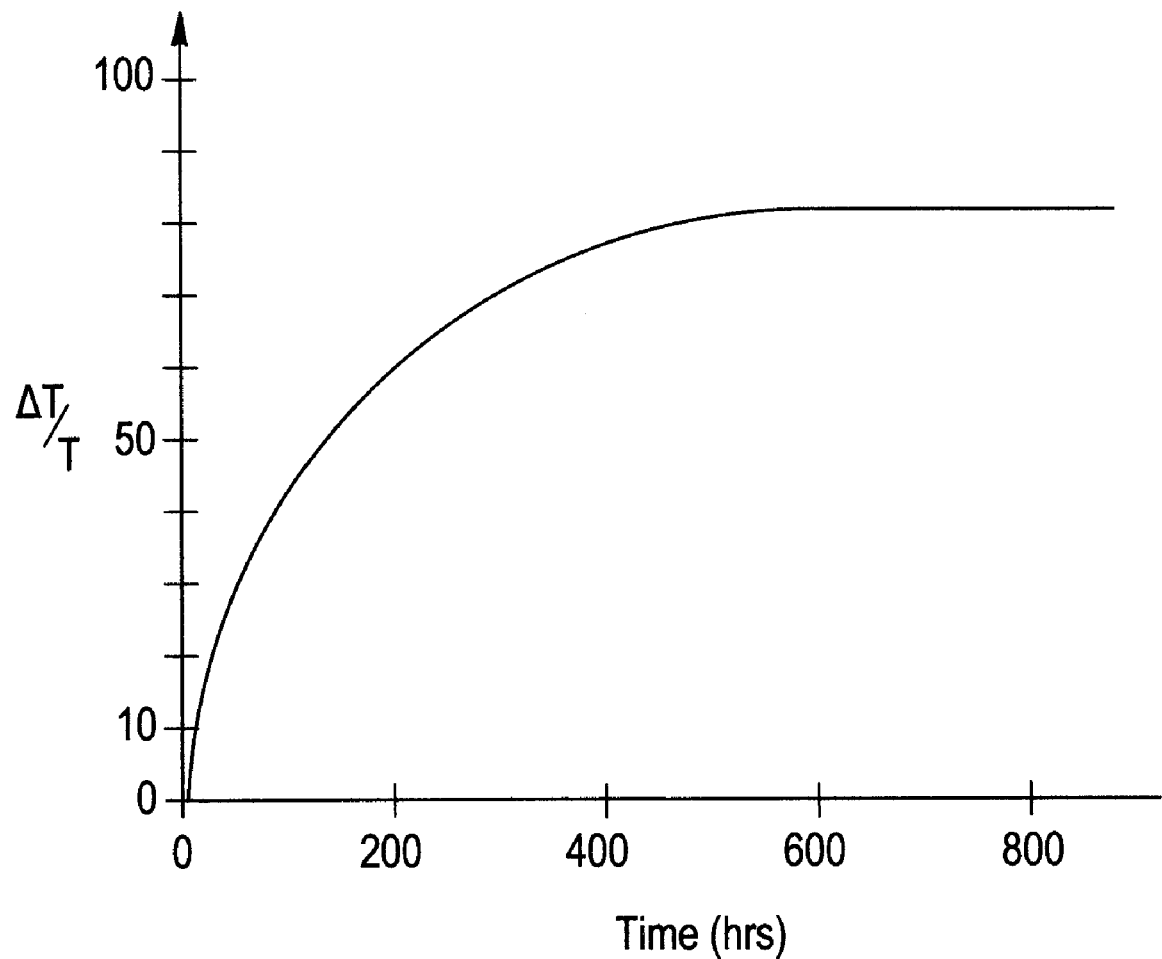
FIG. 2 is a plot of swelling profile of a sample section of a swellable mantle.
Figure 3:
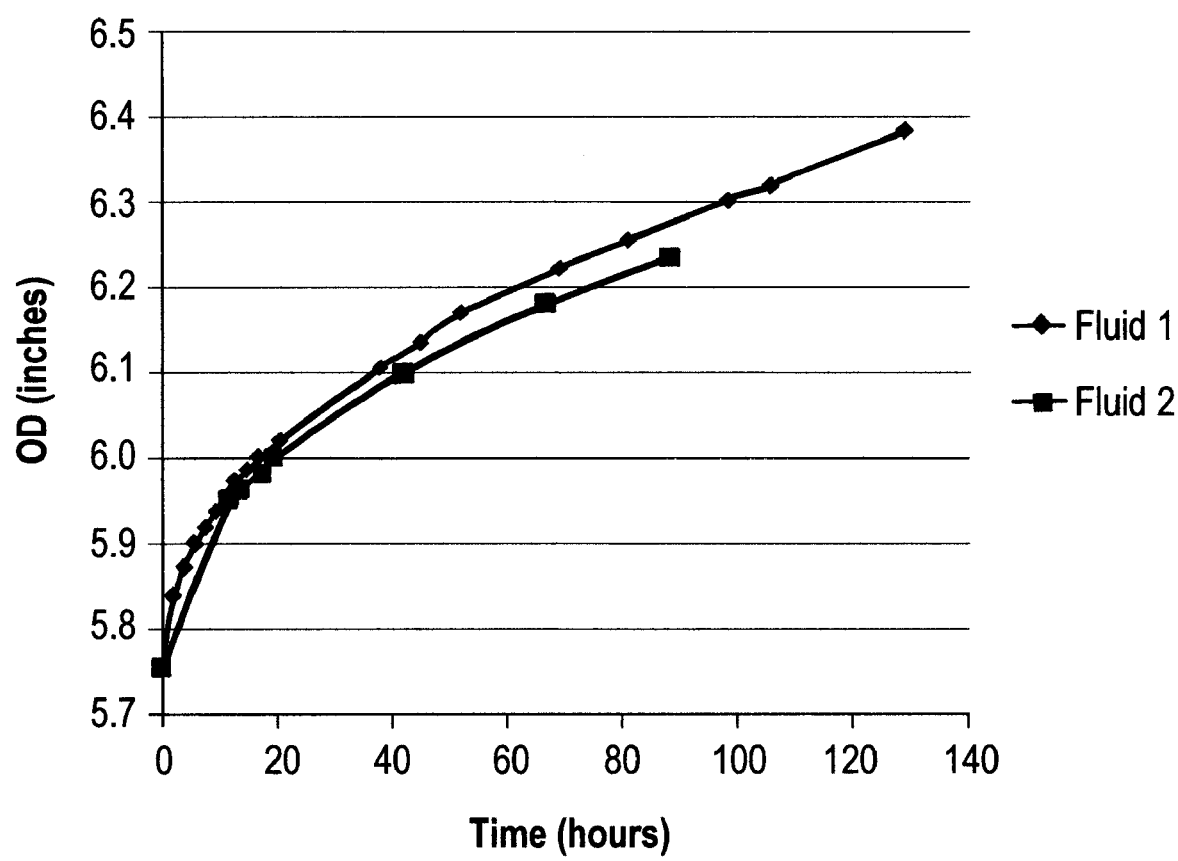
FIG. 3 is a plot of swelling profile of two identical sample sections in different hydrocarbon fluids with the same viscosity.

The test piece 30 is convenient for conducting tests of swell characteristics in an efficient and repeatable manner. The test piece 30 has several advantages over the packer sections 10 of the prior art (and as shown in FIG. 1). Notably, the test piece 30 is simple to manufacture. It is compact and uses a small quantity of swellable material. This facilitates the production and storage of large numbers of test pieces 30, optionally with different swellable materials 34. The test piece is portable and facilitates use in compact swell testing apparatus. The substrate provides support to the swellable material and allows consistent production of samples. It is envisaged that for each batch of swellable material delivered to a manufacturer of oilfield equipment, a number of test pieces could be created for testing the swellable characteristics before deployment of manufactured equipment, or stored for use in post-deployment testing.

Figure 6:
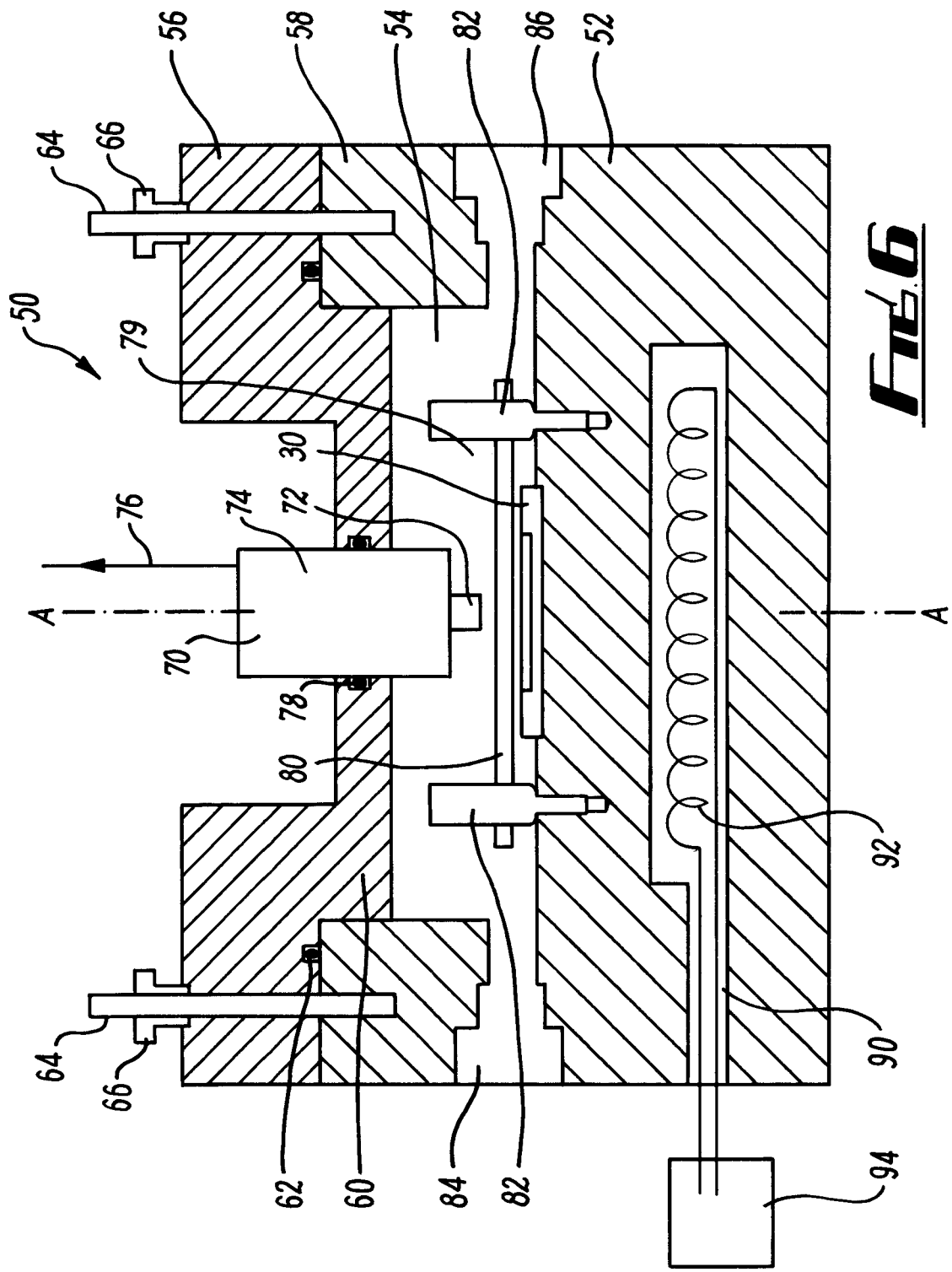
FIG. 6 is a sectional view of a testing apparatus in accordance with an embodiment of the invention.

FIG. 6 shows a testing apparatus in accordance with an embodiment of the invention. The apparatus, generally shown at 50, is configured for testing a swell characteristic of a swellable material used in oilfield equipment. The apparatus has particular application to testing of the test pieces 30 described with reference to FIGS. 4A and 4B, but it will be apparent to one skilled in the art that the testing apparatus 50 may also be used with different test pieces.

The apparatus 50 comprises a substantially cylindrical body with longitudinal axis A, and is shown in FIG. 5 in longitudinal section. The body comprises a base section 52 and a cap section 56, which together define an internal chamber 54. The base section 52 and the cap section 56 are formed from a suitable metal such as stainless steel. The cap section 56 fits onto an annular wall 58 which up stands from the base section 52 to define the internal chamber 54. The apparatus 50 is substantially symmetrical about a longitudinal axis A, with fasteners 64 circumferentially distributed around the apparatus to fix the cap section 56 to the base section 52 and close the chamber 54. The fasteners 64 are securing pins which extend through co-aligned bores in the cap section and the annular bore 58, with threaded portions cooperating with thumb screws 66. Other securing means can be used in alternative embodiments of the invention. A central portion 60 of the cap section 56 extends into the inner diameter defined by the annular wall 58. An o-ring 62 is provided between the upper surface of the annular wall 58 and the lower surface of the cap section 56 to create a fluid seal with the interior of the chamber.

The apparatus 50 comprises a transducer 70 extending through a central aperture in the cap section 56 from the outside of the apparatus into the internal chamber 54. In this embodiment, the transducer 70 is an eddy current transducer, such as Micro-Epsilon Group's DT3010-A series of sensors. An o-ring 78 is provided between the transducer body 74 and the cap section 56 to provide a fluid seal with the chamber 54.

The apparatus 50 is configured to receive a test piece 30 as described with reference to FIGS. 4A and 4B in a mounting assembly, generally shown at 79. The test piece 30 is located on a surface of the base section 52 beneath a target plate 80, formed in this case from aluminium. The target plate 80 is mounted to the base section 52 via hexagonal pillars 82, which allow vertical movement of the plate (in the direction of the axis A) but are keyed with the plate to prevent relative rotation. The transducer 70 is located at a distance of approximately 5-10 mm from the target plate 80, although the position of the transducer may be adjusted, for example by a micrometer adjuster (not shown), to take account of desired operational parameters of the particular eddy current transducer used.

The transducer 70 tracks vertical movement of the target plate through proportional changes in the eddy current between the transducer sensor head 72 and target plate 80 as the position of the target plate 80 moves upwards in the direction of the axis A. The transducer 70 outputs this as measurement data via line 76.

The apparatus comprises an inlet 84 and an outlet 86 to the fluid chamber 54. The inlet allows delivery of fluid into the chamber 54. The inlet 84 and the outlet 86 are provided with connectors for connection with a suitable fluid delivery system such as a fluid hose. A fluid inlet and outlet allows continual circulation of fluid. This allows a fluid to be exchanged or circulated out of the apparatus during the measurement process, as will be described below. In an alternative embodiment, the fluid outlet may be sealed during use, and the fluid inlet may be in communication with the reservoir to ensure that there is an adequate supply of fluid to the fluid chamber. In other embodiments, the fluid chamber may be filled with fluid prior to commencement of the test, with the fluid supply disconnected and the fluid chamber plugged.

The apparatus 50 is also provided with a thermal regulation system 90. In this embodiment, the thermal regulation system 90 comprises a joule heater 92 disposed in the base section 52 and coupled to a temperature controller 94. The heater 92 allows the apparatus 52 to be operated at elevated temperatures to simulate the conditions in a downhole environment. In other embodiments, the system 90 may include alternative heating and/or cooling elements such as Peltier devices. Optionally, a temperature sensor such as a thermocouple may be provided in the chamber 54 for measurement of the internal temperature of the apparatus. The measured temperature may be fed back to a temperature controller. Insulating cladding may also be provided on the exterior of the apparatus to improve heat retention.

In use, the chamber 54 is filled with a fluid and the test piece 30 is exposed to the fluid. Any increase in volume of the swellable material in the test sample 30 due to exposure to the fluid causes the target plate 80 to be displaced vertically. This displacement is measured by the transducer 70, with the measurement signal output from the apparatus via line 76. The apparatus therefore allows regular, automated measurement of the swelling of the swellable material in the test sample. The swell characteristic is measured in situ, while the test sample is exposed to the fluid, and avoids the need for interruption of the test. The apparatus is capable of measuring an increase in thickness of the test sample automatically with no manual intervention by a user. This increases the consistency of the measurement. The transducer is also capable of measuring the increase in thickness with a high degree of precision, reducing errors caused by calliper measurement. The transducer and measurement system may be configured for continuous measurement of the transducer, or measurement at regular sample intervals. This increases the quality of the measurement data.

Figure 7:
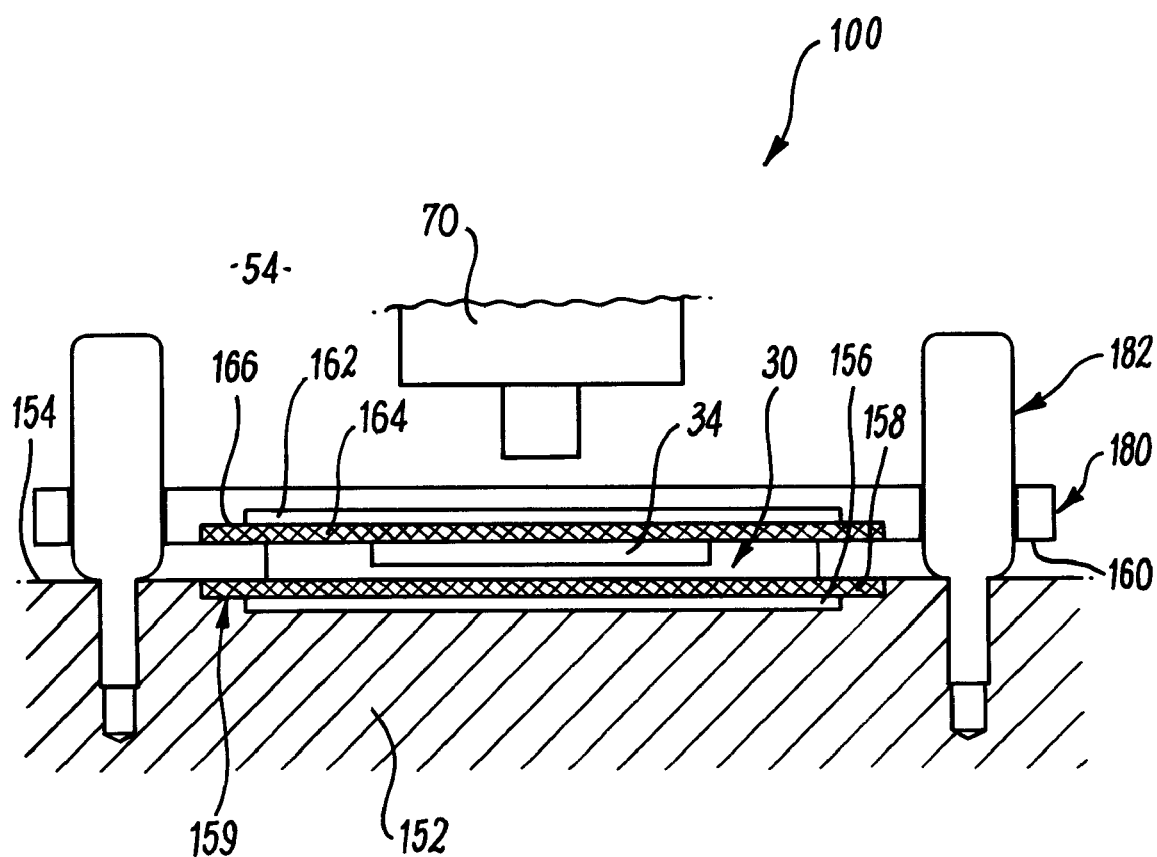
FIG. 7 is a sectional view of a testing apparatus in accordance with an alternative embodiment of the invention.

FIG.7 is a sectional view through a mounting assembly 100 of an apparatus in accordance with a preferred embodiment of the invention. The apparatus in which the mounting assembly 100 is located is similar to, and will be understood from the arrangement 50 shown in FIG.6. The transducer 70, fluid chamber 54 and lid section (not shown) are substantially identical to the embodiment of FIG.6. However, the mounting assembly 100 increases the fluid exposure of the test piece 30.

Shown in FIG.7 is a part of the base section 152, which is similar to the base section 52 of apparatus 50. The base section 152 differs in that it is provided with a recess 156 in its upper surface 154. The recess 156 is sized to receive a porous layer 158, which is formed from a metallic mesh material. An annular ledge 159 is provided around the perimeter of the recess 156 and supports the porous layer 158 above the bottom of the recess. The porous layer 158 provides a support for the test piece 30. The mesh of the porous layer provides a network of pores which allow fluid flow through the layer 158 and around the recess 156.

As with the embodiment of FIG.6, the target plate 180 is mounted on hexagonal pillars 82 which permit vertical movement of the support plates, but prevent relative rotation.

The target plate 180 is provided with a similar recess 162 on its lower surface 160. The recess 162 is sized to receive a porous layer 164, which is supported from the base of the recess 162 by an annular ledge 166. The arrangement allows fluid communication from the fluid chamber 54 to the recess 162, via the porous layer 164. The upper surface of the swellable layer 34 is therefore exposed to fluid in the support layer 64 and recess 162, and the recesses and porous layers provide a complete fluid circulation path around the test piece, improving fluid access to the swellable material 34.

In an embodiment of the invention, the apparatus of FIGS. 6 and 7 is used as follows. The test piece 30 is located in the fluid chamber 54, and the fluid is delivered to the chamber via the inlet 84. The test piece 30 and the swellable material 34 in fluid communication with the fluid in the chamber, and depending on the nature of the swellable material and the type of fluid, this exposure may trigger a change in volume of the swellable material 34. An increase in volume will be manifested as a change in thickness and thus the upper surface of the swellable material 34 will impart a force on to the target plate, which in turn will be measured by the eddy current transducer 70. Changes in thickness are therefore detected by the transducer, and the measurement signal can be output as a time series via line 76. The time series data is recorded in a data storage means in communication with the apparatus, which forms part of a personal computer. Alternatively, or in addition, the data may be directly output to a display to a user. The apparatus and method therefore enables a series of measurements of the thickness of the swellable material over time to be collected.

Figure 8:
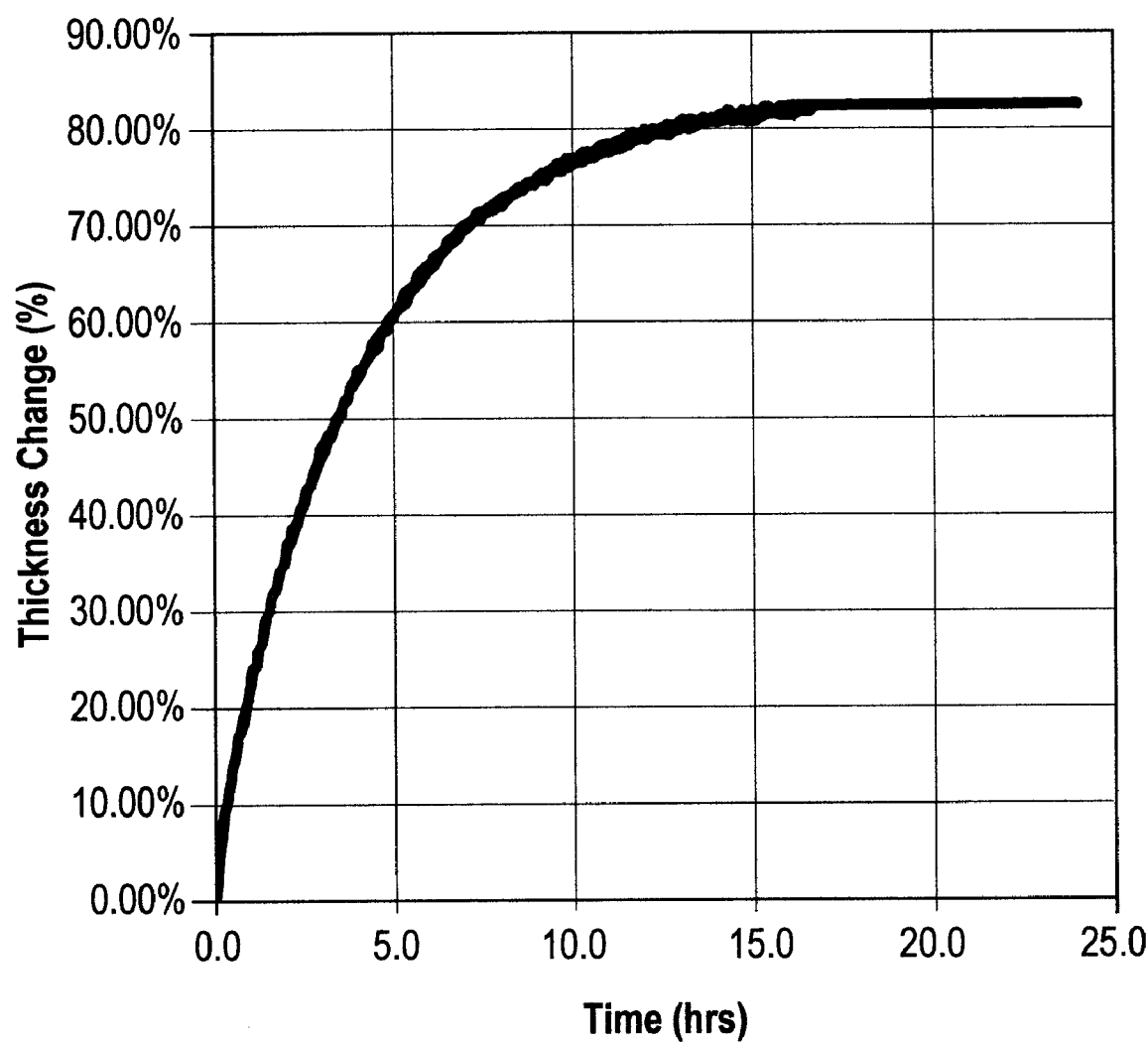
FIG. 8 is a plot of thickness change versus time for a test piece of an embodiment of the invention.

A typical measurement data set is plotted in FIG.8, with the change in thickness is plotted as a percentage of the initial thickness (i.e. $\Delta T/T$, where T is the initial thickness and $\Delta T$ is the cumulative change in thickness). The plot shows an initial increase of the thickness of the material during hours 0 to 5 at a relatively fast rate, with a gradual reduction of the rate of change during hours 5 to 15 and a levelling off from approximately hour 16.

Figure 9:
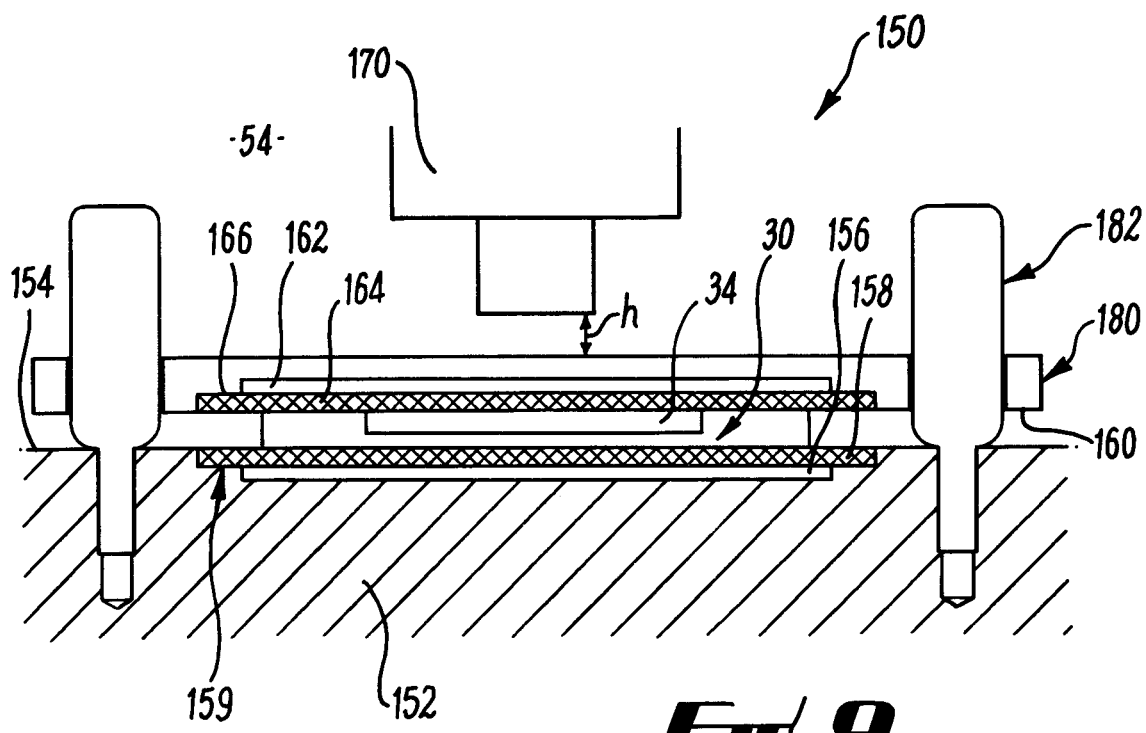
FIG. 9 is a sectional view of a part of a testing apparatus in accordance with a further alternative embodiment of the invention.

The testing apparatus described above is configured for the measurement of thickness data by using a contactless eddy current transducer 70 to measure the vertical displacement of a target plate. In an alternative embodiment, the testing apparatus is configured for measurement of a pressure exerted by a support plate on a transducer. FIG.9 is a cross-sectional view of a part of an apparatus 150 in accordance with such an alternative embodiment of the invention. The testing apparatus 150 is similar to the testing apparatus 50, with like-parts indicated by like-reference numerals. However, the apparatus differs in the nature of the transducer, which in apparatus 150 is a pressure transducer 170 which is located at a fixed distance h above the target plate 180 when the test piece 30 is in an unswelled condition. An example of a suitable transducer is Impress Sensors & Systems Limited's DMP 343 low pressure transducer. The distance h is selected to correspond to a separation distance between the outer surface of a swellable component of a tool before swelling and the surface with which it seals (i.e. the swelling distance before contact). In the case of a swellable packer, this is the radial depth of the annular space between a swellable tool and a surrounding wall.

As an example, a swellable packer having an initial mantle thickness of 0.6275 inches (about 15.9 mm), may be configured to run on a base pipe or mandrel with outer diameter of 4.5 inches (about 114.3 mm), in a wellbore having inner diameter of 6.125 inches (about 155.6 mm). The annular space between the mandrel and wellbore therefore has a radial distance of 0.8125 inches (about 20.6 mm), and the required change in thickness of the swellable mantle for wellbore contact is 0.1875 inches (about 4.8 mm) or around 30% of the original thickness of the swellable mantle. For the test configuration of FIG.9, the separation distance of the support plate and the pressure transducer is calculated in proportion. If the initial thickness of the swellable material 34 is 0.080 inches (about 2.0 mm), the distance h is 0.024 inches (about 0.6 mm) for an equivalent thickness change of 30%. The distance h is configurable in the testing apparatus.

In use, the test piece 30 is exposed to a fluid delivered to the chamber. The fluid triggers an increase in volume of the swellable material 34 and a vertical displacement of the target plate. When the support plate has displaced by distance h, it is brought into contact with the transducer and exerts pressure on the transducer. The pressure is measured and output via line 76. The data may be output as a time series of measured pressure data. Continued swelling of the swellable material will tend to increase the pressure on the transducer, until further swelling of the material is prevented by a back pressure from the transducer. The point at which the test sample exerts a maximum pressure on the transducer (which corresponds to the pack-off time) can be determined from the measurement data.

Figure 10:
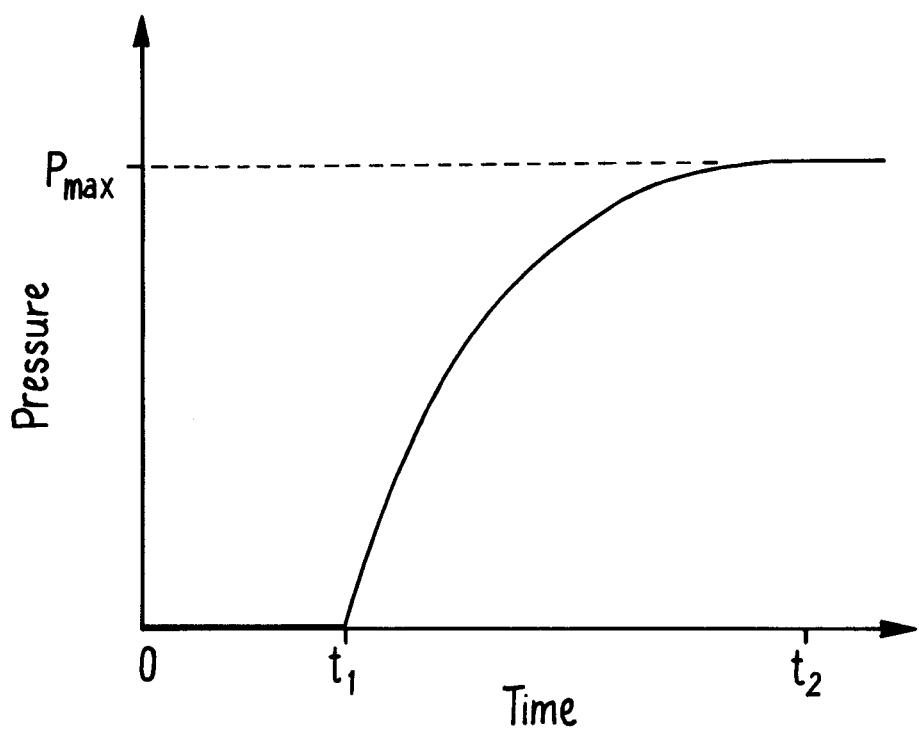
FIG. 10 is a plot of pressure versus time measured using the apparatus of FIG. 9.

FIG.10 is a typical plot of pressure data versus time using the testing apparatus of FIG.9. Between a time of t=0 and t=t1, the pressure measured by the pressure transducer is zero, because the support plate has not been brought into contact with the transducer 170. At time t1, the plate 180 has moved to the distance h, and the plate contacts the transducer. As the swellable material of the test piece continues to swell, the pressure transducer measures an increase in pressure between times t1 and t2. The rate of increase of pressure reduces, until at t2, a maximum pressure, Pmax has been reached: t2 therefore represents the pack-off time described above. In practice, it may be preferred to calculate a "guaranteed pack-off time" which is greater than t2. A guaranteed pack-off time may be calculated by multiplying t2 by a factor (for example 1.5) or adding a minimum additional time to t2.

Measurement data sets collected by the swell tests described above may be used to predict a swelling characteristic of a swellable component of downhole equipment. For example, the test piece data may be compared with measurement data from the swelling of a packer or packer section to derive a relationship between the swelling rates of the test piece and the packer. The relationship can then be used to predict the swell characteristics, such as the contact time and the maximum pressure) of the packer. Data from a new test on a test piece, for example using a fluid sample recovered from a wellbore, can be input into the derived relationship in order to calculate the predicted swell characteristics of the packer.

Figure 11:
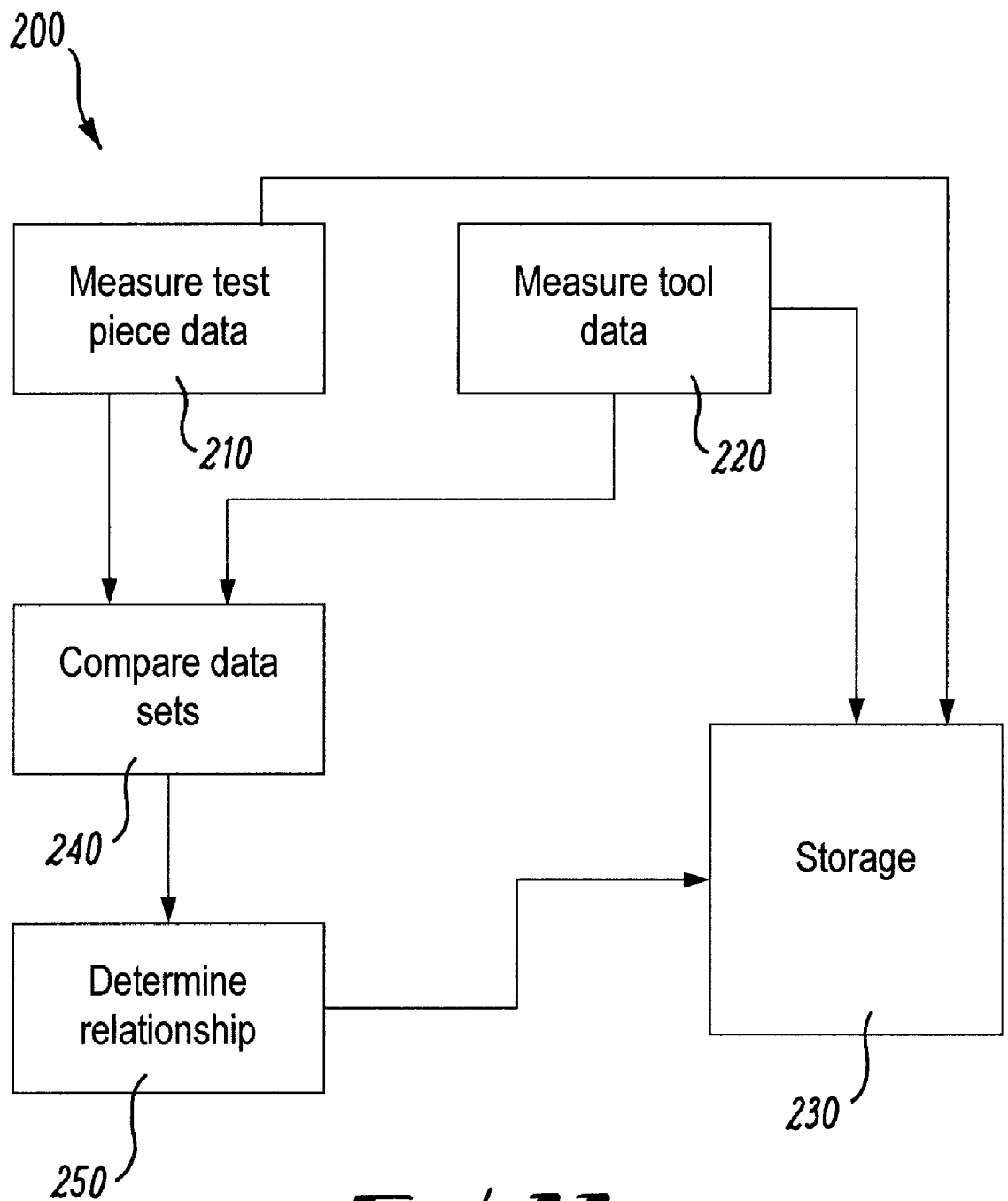
FIG. 11 is a block diagram showing schematically the steps of a method of collecting test data in accordance with an embodiment of the invention.

FIG.11 is a block diagram which schematically shows a method 200 for collecting test data for use in analysis of swelling characteristics. In step 210 a test piece measurement data set is collected from a test piece exposed to a reference fluid, using the method and apparatus described above. In step 220, a tool measurement data set is collected by exposing a tool, or a sample section of a tool, to the same reference fluid used in step 210. It should be noted that in step 220, the tool measurement data set need not be measurement of data of the complete tool itself, but may be a measurement of the swell characteristics of a sample section generally considered to correspond to the swell characteristics of the tool, for example the sample packer section described with reference to FIG.1. In this embodiment the tool is a swellable packer, and the tool measurement data set is collected by measuring a packer section as described with reference to FIG.1.

The respective measurement data sets are stored in a database 230 as time series of measurement data. As described above, the measurement data may be thickness data or pressure data, or a combination of the two. In step 240, the measurement data sets are compared, using any of a number of conventional statistical techniques. The comparison may be performed using software on a personal computer or in a dedicated processing module. In step 250 a relationship between the swell profile of the test piece in the reference fluid and the swell profile of the tool in the reference fluid is determined from the comparison of data. The determined relationship is stored in a database, for later use in predicting the swelling characteristics of a tool.

One example of a relationship between a test piece data set and tool data sets is by a numerical time domain scaling multiplier S. Such a multiplier may be applied to a time value of the test piece swell data, such that the swell profiles match one another. Such an operation is equivalent to rescaling the time axis for a plot of the percentage thickness change against the time value data. Time domain scaling multipliers may be calculated by any of a number of statistical or numerical processing techniques. One simple method involves optimising the scaling multiplier to minimise a difference between the scaled and unscaled time series. Any of a number of different optimisation techniques may be used. One simple method includes the steps of: setting a starting value to a time domain scaling multiplier; applying it to time values of the test piece data for each data point; replotting the thickness change data for the test piece against the rescaled time axis; calculating a difference between the respective swell profiles of the rescaled test piece data and the tool data; and perturbing the time domain scaling multiplier. The new time domain scaling multiplier is applied to the time values of the testpiece data for each data point, and the thickness change data for the test piece is replotted against scaled time axis. A difference between the respective swell profiles of the rescaled test piece data and the tool data is calculated, and compared with the previously calculated difference. The process can be repeated until the difference between the respective plots is minimised.

Figure 12:
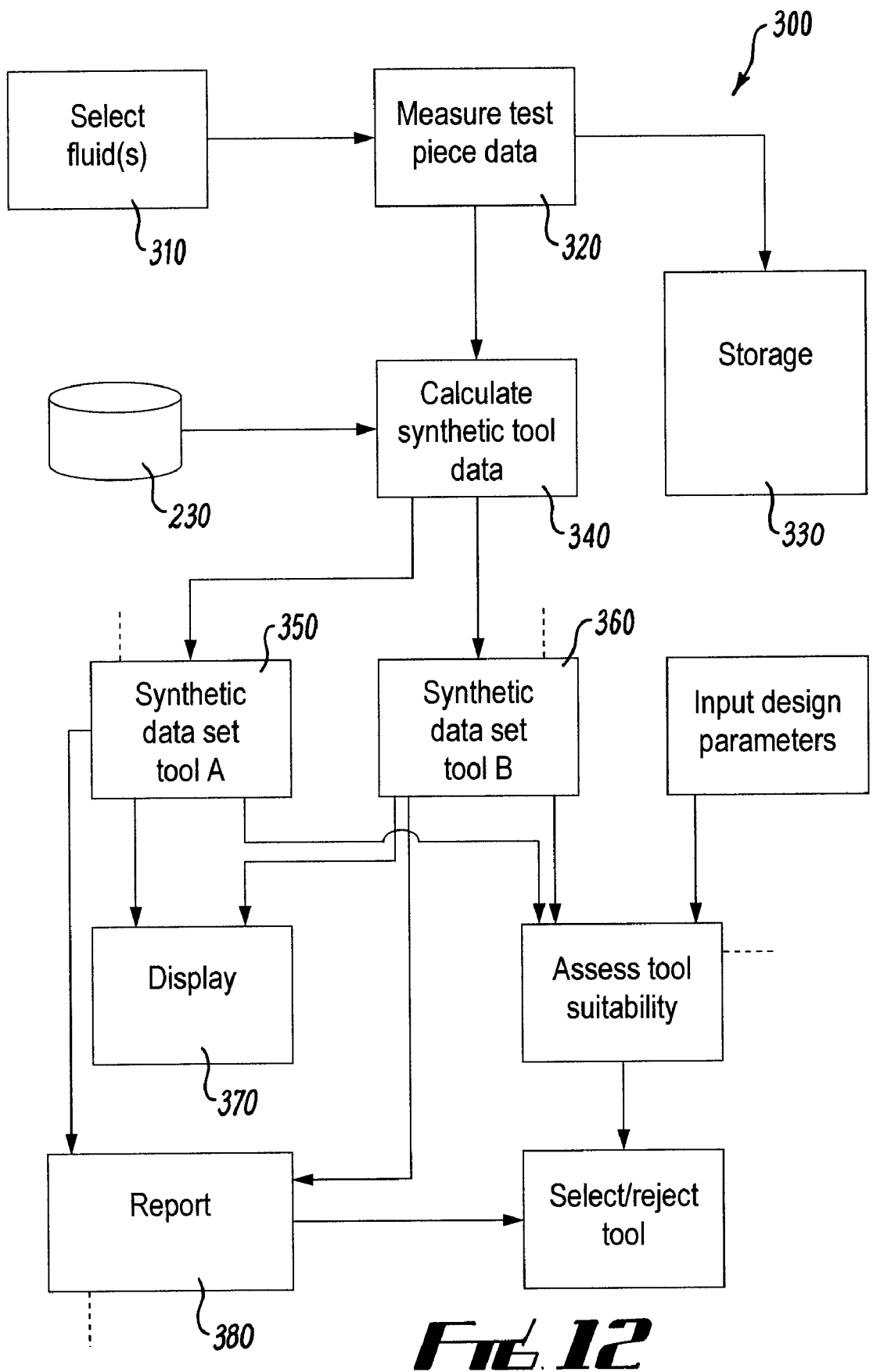
FIG. 12 is a block diagram showing schematically the steps of a method of predicting a swell characteristic of a tool in accordance with an embodiment of the invention.

FIG.12 is a block diagram which schematically shows a method 300 that uses a determined relationship from the method 200 to predict the swell characteristics of a swellable component or swellable tool. In step 310, a fluid sample is selected and provided in the test apparatus 50. This may be an actual fluid sample from the wellbore environment in which a tool is planned to be deployed. Alternatively, it may be a fluid representative of the fluid in the wellbore environment, for example a synthesised fluid to approximate the fluid conditions expected in the wellbore. It may also be a combination of fluids, and may be a number of separate volumes of different fluids to which the test piece will be exposed during different parts of the test, as will be described in more detail below.

The test piece is subject to the test in step 320 as described with reference to FIGS. 6, 7 and/or 9 above, and the test piece measurement data is output as a time series and recorded in a data storage apparatus 330. Optionally, a display representative of the swell characteristic from the measurement data set may be generated and displayed to a user. For example, the test piece swell profile can be displayed to a user in real time via a graphic display (not shown).

The test piece data set is then used in step 340 to calculate the predicted swell profile of one or more tools. This is carried out by applying to the measured test piece data the relationship between a test piece swell profile and a tool swell profile determined using the method of 200. This may be for example the time domain scaling multiplier S, as described above. Synthetic tool datasets 350, 360 are generated for each tool design for which a relationship (or multiplier S) has been determined. Each synthetic tool dataset represents the predicted swelling behaviour of the respective tool in the sample fluid. Swelling profiles can be output as a time series of swell data to a data storage apparatus 330, and/or can be displayed (step 370) to a user via graphical display. The information can be used to generate (at step 380) a report on the swelling behaviour of the specific tool designs in the sample fluid. For example, the report may include a predicted contact time for a swellable packer and/or a predicted pack-off time. In certain embodiments of the invention, the report also provides an expected pack-off pressure, which may be used in conjunction with information on the surface area of the packer and the expected co-efficient of friction with the surrounding wall, to derive information representative of the pressure capability of the packer.

Optionally, the method may include the additional steps of selecting or recommending a particular tool design, according to desired swell parameters input into the system at step 390. For example, an operator may input a maximum initial outer diameter of a packer, and may specify a minimum contact time. Alternatively, a user may specify a fixed base pipe size, and/or may require that the tool must have a pack-off time not greater than a particular value. The system is capable of providing a synthetic swell profile data for a number of specific tool designs in a sample fluid, and then assisting a user with the selection of the tool design for the specific application.

Figure 13:
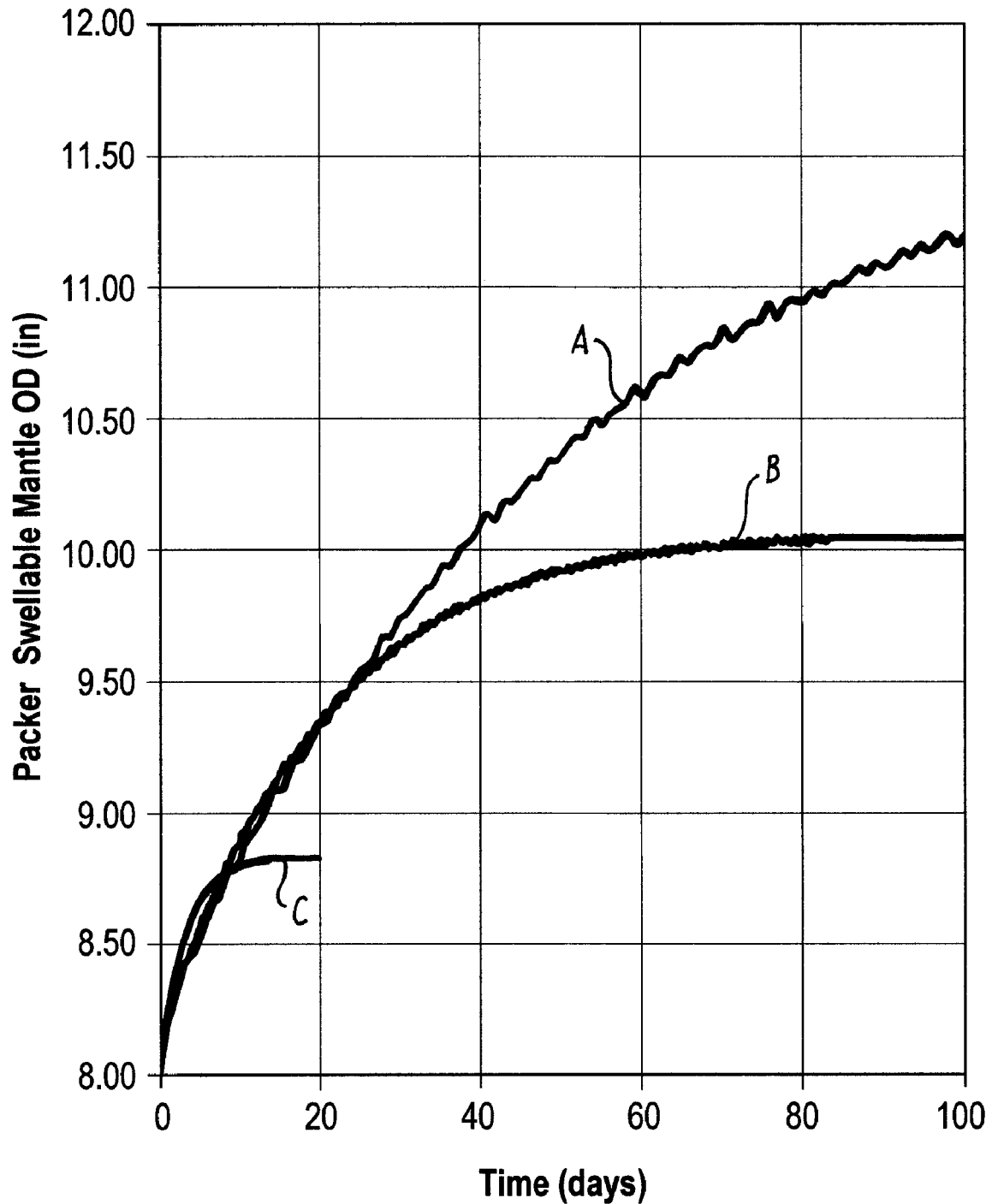
FIG. 13 is a plot of predicted swell profiles of tools with different configurations.

FIG. 13 shows the predicted swell profiles of a number of different tool designs calculated using the method 300. Plot A shows schematically the predicted swell profiles for three wellbore packers having the same initial outer diameter of the swellable mantle, and different size base pipes. The Figure shows graphically how the method can be used to select or eliminate particular tool configurations (which in this case are base pipe diameters) depending on constraints on swelling time and/or final OD of the packer.

The method 200 can be repeated to obtain a number of different time domain scaling multipliers S for different tool configurations. It is then possible to determine a relationship between the time domain scaling multipliers and various parameters of the tool configuration. For example, a relationship can be derived which describes the dependence of time domain scaling multipliers on the ratio of test piece thickness to test packer element thickness, by plotting calculated scaling multipliers against the ratios of the packer swellable mantle thickness $T_p$ to the thickness of the test piece $T_c$. Using standard statistical techniques, it is possible to determine a relationship, for example a quadratic relationship in the form $$S = aR^2 + bR - c \quad \text{(Equation 1)},$$

where R is $T_p/T_c$, between the scaling multiplier S and the tool parameters.

The invention therefore provides a method by which swell profile information for a proposed new packer size can be obtained on the basis of the derived relationships and the measurement data from a test piece. For the proposed packer design, the appropriate time domain scaling multiplier can be derived from of the ratio of the test piece thickness and the thickness of the swellable member in the packer. This is then applied to the swell test data measured from a test piece to obtain a predicted swell profile of the packer design.

The techniques described above can be applied to a measurement of pressure exerted by the swellable member during an increase in volume. Again, the time series pressure data are collected for a test sample, and compared with the time series of pressure data collected using the conventional testing of a packer section to derive a relationship between the swelling profiles.

One specific example of the method 200 of the invention is described here. In this example, a test piece 30 was tested using the apparatus 50 in order to obtain a time series of test piece data which corresponds to thickness changes of the swellable material. The test piece 30 was exposed to a fluid sample selected to approximate the fluid encountered in the wellbore into which it is planned to run a packer. The temperature of the fluid was maintained at a constant 80° C.

Figure 14:
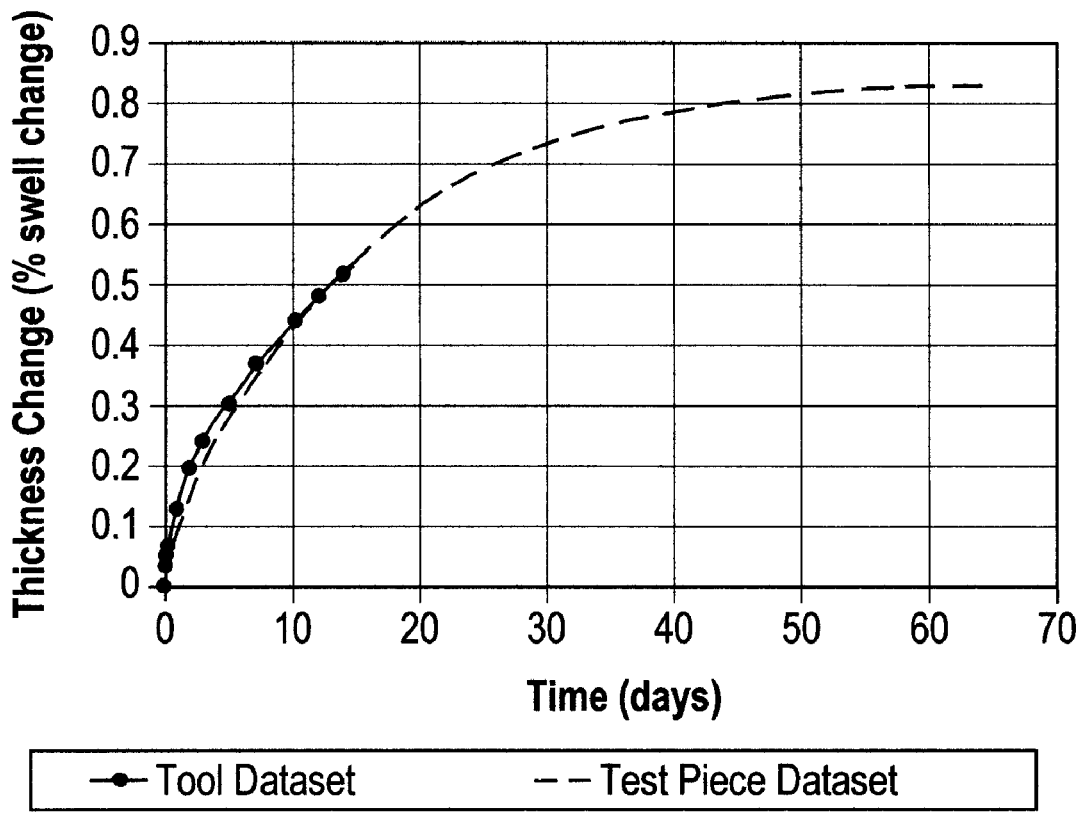
FIG. 14 is a plot of tool measurement data and rescaled test piece measurement data.

A wellbore packer sample section, similar to section 10 shown in FIG. 1, was placed in a fluid bath containing the same reference fluid, also maintained at a temperature of 80° C. The sample section was a packer section having a 4.5 inch (about 114.3 mm) base pipe with a swellable mantle which had an outer diameter of 5.5 inches (about 146.1 mm). Measurements were taken manually using a calliper gauge over a period of days to obtain a tool measurement data set. The test piece data set and the tool data set were compared, and it was determined that the data provided a good match when the test piece data had applied to it a time domain scaling multiplier S of 35. In other words, for each data point, a multiplier of 35 was applied to the time value at which the measurement was taken before plotting on the same scale as the tool measurement data. FIG. 14 plots a percentage thickness change against time for the tool (dashed line) and the percentage thickness change of the test piece versus a scaled time, after the time domain multiplier of 35 is applied. The plot shows a close match between the respective plots. The method 200 has therefore been used to determine a relationship between the swelling characteristics of a test piece 30 and the swelling characteristics of a sample section of a packer.

The method 200 was repeated for a number of sample sections of packer elements having different dimensions. In a second example, the test piece data was compared with a data set measured from a sample section of a packer element having a base pipe of 5.5 inches (about 139.7 mm) and a swellable mantle with an initial outer diameter of 8 inches (about 203.2 mm). A comparison of the data sets revealed that a time domain multiplier of 120 led to a correspondence of the swelling profiles.

Similar tests were carried out on a number of different packer configurations, with the results as shown in Table 1.

TABLE 1

| Packer configuration | Base pipe OD (inches) | Mantle OD (inches) | Actual Mantle Thickness $T_p$ (inches) | Test Piece Thickness $T_c$ (inches) | $T_p/T_c$ Ratio | Scaling Multiplier |
|---|---|---|---|---|---|---|
| 7.00 × 8.00 | 7.00 | 8.00 | 0.50 | 0.08 | 6.24 | 20 |
| 7.00 × 8.15 | 7.00 | 8.15 | 0.58 | 0.08 | 7.24 | 30 |
| 4.50 × 5.75 | 4.50 | 5.75 | 0.64 | 0.08 | 7.98 | 35 |

TABLE 1-continued

| Packer configuration | Base pipe OD (inches) | Mantle OD (inches) | Actual Mantle Thickness $T_p$ (inches) | Test Piece Thickness $T_c$ (inches) | $T_p/T_c$ Ratio | Scaling Multiplier |
|---|---|---|---|---|---|---|
| 4.50 × 5.85 | 4.50 | 5.85 | 0.68 | 0.08 | 8.50 | 39 |
| 6.625 × 8.15 | 6.625 | 8.15 | 0.77 | 0.08 | 9.61 | 52 |
| 5.50 × 8.00 | 5.50 | 8.00 | 1.26 | 0.08 | 15.73 | 120 |
| 5.50 × 8.15 | 5.50 | 8.15 | 1.33 | 0.08 | 16.60 | 135 |

The numbers in the first column indicate the packer configuration in notation commonly used in the industry. The outer diameter (OD) of the base pipe and the outer diameter of the swellable mantle are given in inches in columns two and three respectively. The fourth column specifies the actual thickness of the test packer element in inches, as measured. This is the radial thickness of the swellable mantle Tp, which represents approximately half of the difference between the dimensions in columns two and three, with the differences due to engineering tolerances. In all cases, the test coupon thickness Tc was 0.08 inches (column five). The ratio of the radial thickness of the swellable mantle Tp and the test coupon thickness Tc is given in column six, and the derived scaling multiplier, which provides a suitable concordance between the swell profile of the test piece and the swell profile of a packer element, is given in column seven.

Figure 15:
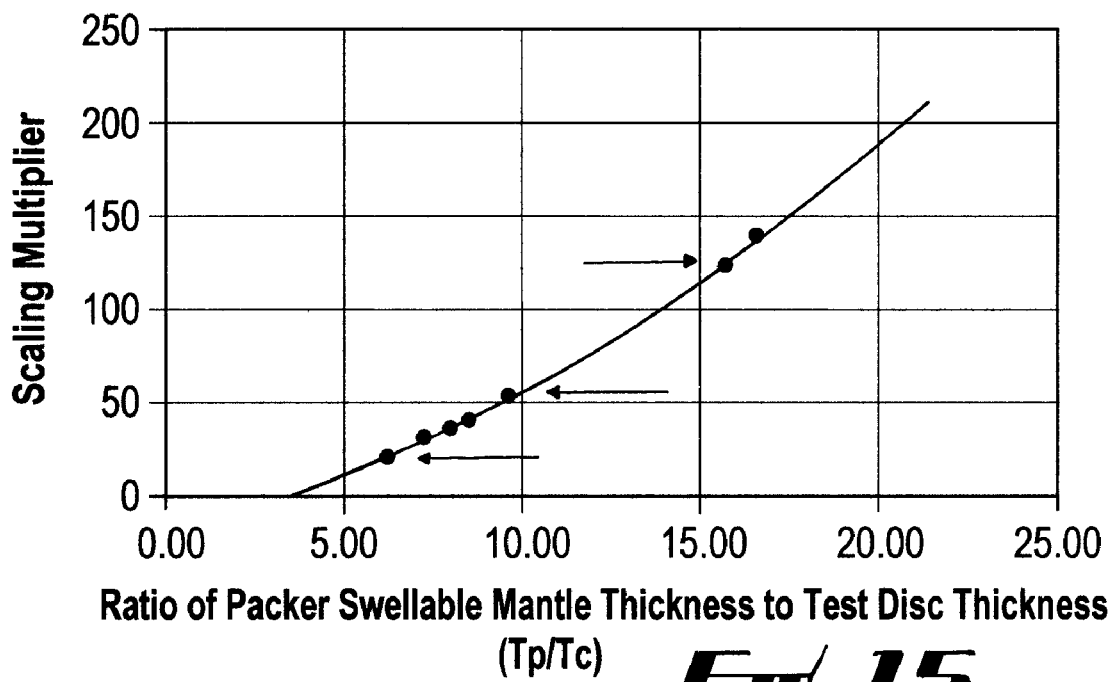
FIG. 15 is a plot of scaling multipliers determined by the method of FIG. 11 against ratio of tool component thickness to test piece thickness.

From the calculation of the time domain scaling multipliers for different ratios of test coupon to test packer element thickness, it a relationship was determined between the time domain scaling multipliers and the ratios. The calculated scaling multipliers were plotted against the ratios of the packer swellable mantle thickness Tp to the thickness of the test piece Tc, with the results shown in FIG. 15. Using standard statistical techniques, a relationship between the scaling multiplier and the thickness ratio was determined to be:

$$S=0.2765R^2+4.5989R-18.94 \qquad \text{(Equation 2)},$$

where S is the scaling multiplier and R is the ratio Tp/Tc.

An appropriate scaling multiplier for the time domain S can now be determined from this relationship for a new proposed packer design, on the basis of the ratio of the test coupon thickness and the thickness of the swellable member in the packer, even where no previous swelling test has been performed on that packer configuration. This is then applied to the swell test data measured from a test piece to obtain a predicted swell profile of the packer design.

Figure 16:
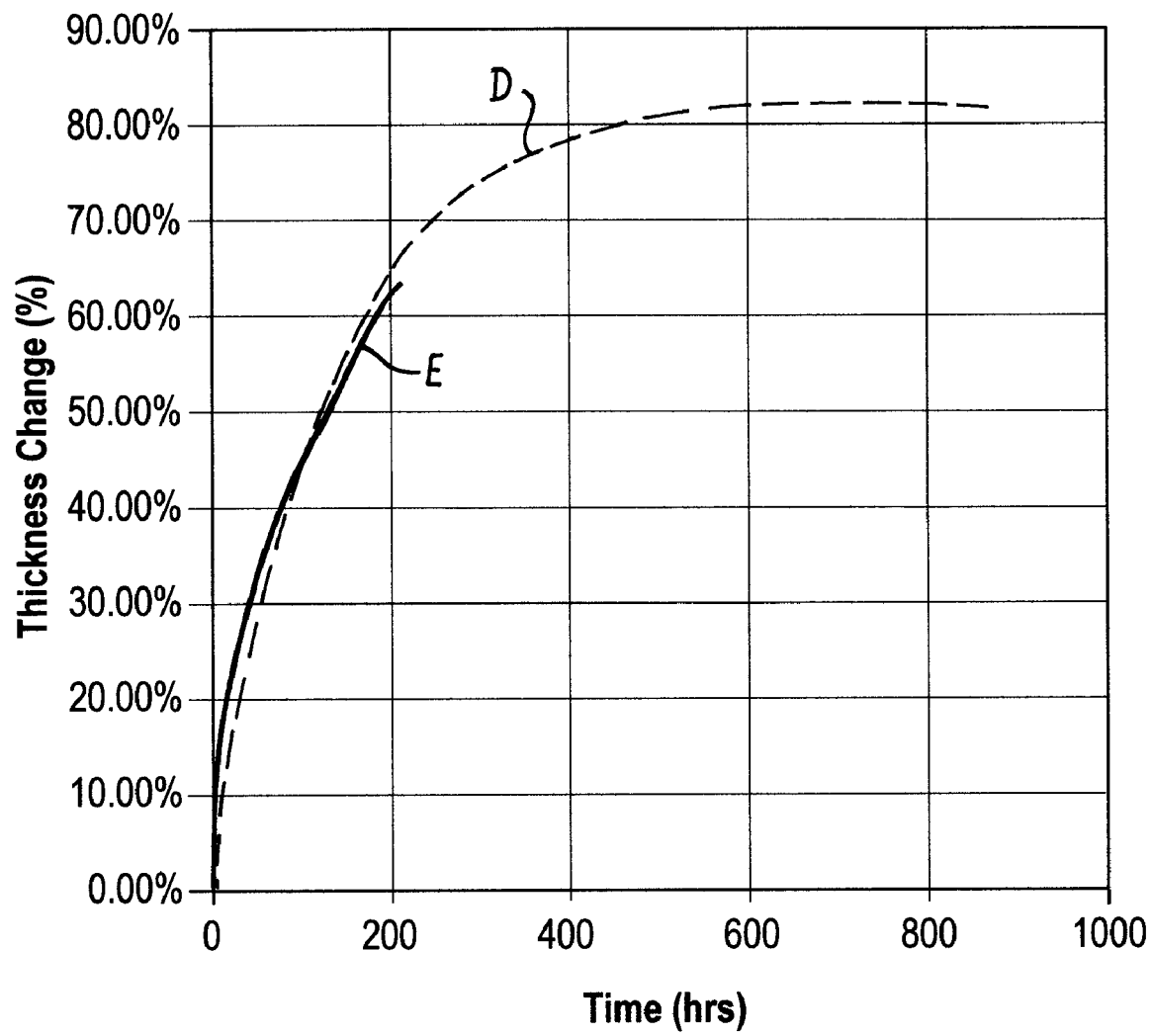
FIG. 16 is a plot comparing a predicted swell profile of a tool with a measured swell profile.

FIG. 16 is a plot of measured data from a tool test and synthetic data for the same tool design calculated using the method 300. In this example, sample packer section tested had a pre-swollen element OD of 5.755 inches (about 146.2 mm) and a base pipe OD of 4.5 inches (about 114.3 inches). The test piece has a rubber thickness of 0.080 inches (about 2 mm). This means the Tp/Tc ratio R is about 7.84, which when input into Equation 2 gives a time domain multiplier S of about 34.14. This is the time domain multiplier that is applied to the test piece measurement data to accurately portray the packer swell profile. The plot shows a high level of concordance with the predicted swell profile, shown by the dashed line D, and the actual measured swell profile, shown by the line E.

The present invention also allows the simulation of different wellbore conditions. For example, during different periods of a swell test, the temperature of the test piece and/or fluid can be varied. The temperature of the test piece could begin at an ambient surface temperature (for example 20° C.) and be gradually increased to simulate an increase in temperature experienced by a swellable packer as it is run to a downhole location and as it is exposed to wellbore fluids. The temperature could be changed rapidly for periods of the test, which may for example simulate the exposure of a packer to a different, cooler fluid (such as an injected fluid stream). Optionally, a temperature sensor such as a thermocouple is provided in the interior of the fluid chamber, or in thermal contact with the test sample. The signal from the temperature sensor may be fed back to the temperature controller. The thermal regulation system 90 may operate in a simple power control mode (similar to a thermostat) or in a continuous variation mode.

The test apparatus also allows different fluids to be circulated passed the test piece during the test. This offers another mechanism for changing the temperature inside the testing apparatus. For example, a fluid at a temperature of 90° C. may be replaced with a fluid at a temperature of 15° C. for a two hour period of the test. The measurement data will be continually to be sampled during the change in temperature.

A fluid of a different nature can be circulated in the testing apparatus. For example, the early stages of a test may expose the test sample to an aqueous fluid or brine, with a later stage of the test exposing the test sample to a drilling fluid or wellbore clean-up fluid. Subsequent stages of the test may expose the test sample to hydrocarbon fluids such as are typically be encountered in the production system. Numerous variations are possible within the scope of the invention. The invention allows the simulation of wellbore conditions likely to be encountered by a typical downhole apparatus. The conditions may be pre-programmed into the apparatus to automatically simulate a fluid circulation schedule for a particular well. Throughout the process, the measurement data is continually taken. Thus the effect on swelling characteristics can be predicted to obtain a swelling profile for the wellbore conditions a tool will experience. A long period of exposure to a hydrocarbon fluid could be interjected with exposure to an aqueous fluid (which may be at a lower temperature) to simulate the injection of a fluid into the wellbore from surface. During such simulation programmes, due account must be given to the time domain relationship between the swell profile of the test piece and swelling profile of the packer, for example by dividing the typical time for which the packer would be exposed to a particular fluid in a wellbore operation by the time domain scaling multiplier to obtain a time for which the test piece should be exposed to that fluid during the test.

Figure 17A:
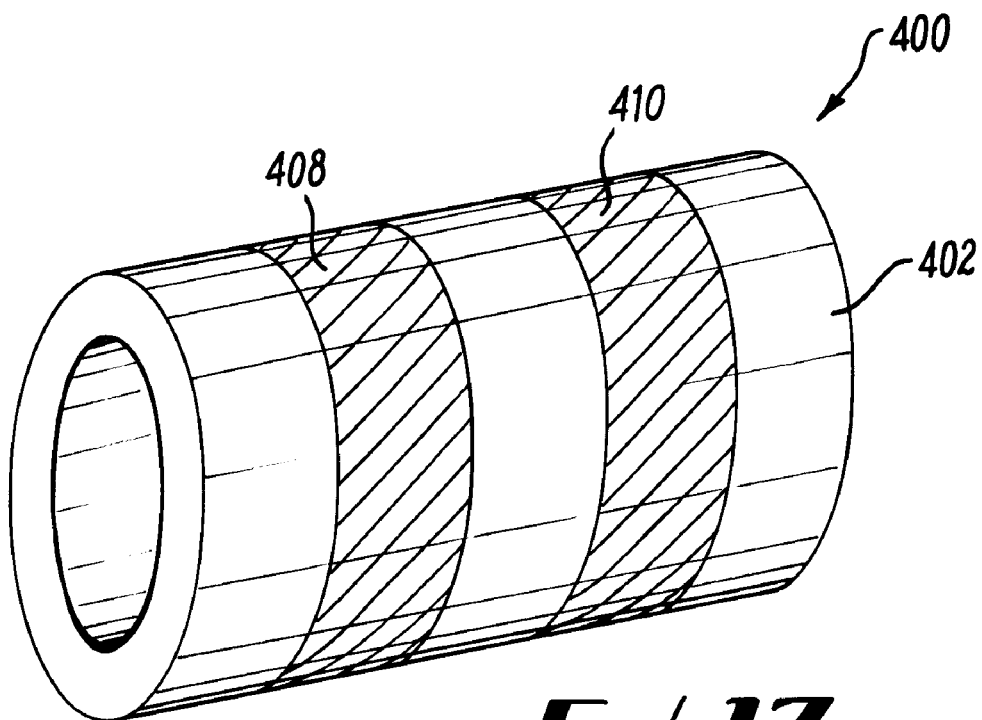
FIGS. 17A and 17B are respectively perspective and sectional views of a packer sample section in accordance with an embodiment of the invention.
Figure 17B:
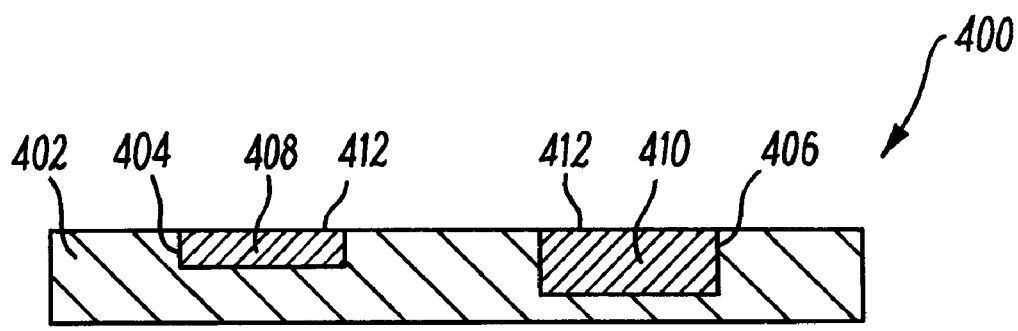
Figure 17B:

The above-described embodiments of the invention relate the swelling characteristics of a test piece with swelling characteristics of a sample packer section 10 which is representative of the swelling of a swellable wellbore packer. FIGS. 17A and 17B illustrate an alternative sample section which may be used with certain embodiments of the invention. The sample section, generally depicted at 400, comprises a cylindrical base pipe 402 formed from a metal such as steel. Machined into the outer surface of the base pipe are annular recesses 404, 406. Recess 404 is formed to a first depth, and recess 406 is formed to a second depth, greater than the first depth. Located in the recesses is swellable material selected to increase in volume on exposure to the wellbore fluid, which in this case is EPDM rubber. The swellable material creates swellable bodies 408 and 410 which fill the recesses to provide an outer surface 412 which is flush with the surface of the pipe 402. The swellable bodies are bonded to the pipe 402 on their lower surfaces and on the radially extending side walls of the recesses.

The sample section 400 has certain advantages over the sample section 10 of the prior art. Firstly, the swellable bodies have a swelling behaviour which more closely resembles the swelling of a swellable member of a wellbore packer. By bonding the lower and side surfaces of the swellable bodies onto the base pipe, the swellable bodies resembles the form of a swellable packer, which is typically bonded on its lower surface to a base pipe, and to gauge rings or end rings which are upstanding from the base pipe to abut the radially extending surfaces which define the ends of the swellable member. In contrast, with the sample section 10, the ends of the swellable member 12 are exposed to the wellbore fluid, which increases the surface area to volume ratio at the opposing ends of the sample section 10 and creates non-uniform swelling which is not characteristic of a typical wellbore packer configuration. The sample section 400 thus more closely resembles the structure of a typical wellbore packer. Forming the swellable bodies in annular recesses also provides advantages in the manufacturing process. The swellable material which makes up the swellable bodies can be applied, moulded, compressed and bonded into the recesses, and the outer surface of the bodies can be easily machined to be flush with the outer diameter of the pipe 402.

The recesses 404 and 406 are formed to different depths, to form corresponding swellable bodies 408, 410 with different thicknesses. This facilitates the simultaneously testing of swellable bodies which correspond to packers of different dimensions. Although two recesses are formed in the sample section 400, a single recess may be provided in an alternative embodiment, and other embodiments may comprise three or more recesses. Different recesses may be formed with different depths and/or shapes, and the swellable bodies with different swellable materials may be provided in different recesses on the same sample section. It will also be appreciated that the sample section may be formed on a solid mandrel, in place of the base pipe 402. The mandrel or base pipe may be provided with formations to facilitate handling of the sample section.

The invention also contemplates that a measurement data set could be obtained from a full scale trial of downhole equipment. For example, a full scale packer could be deployed in a test bore, with regular outer diameter measurements taken in order to provide reliable measurement data.

Figure 18:
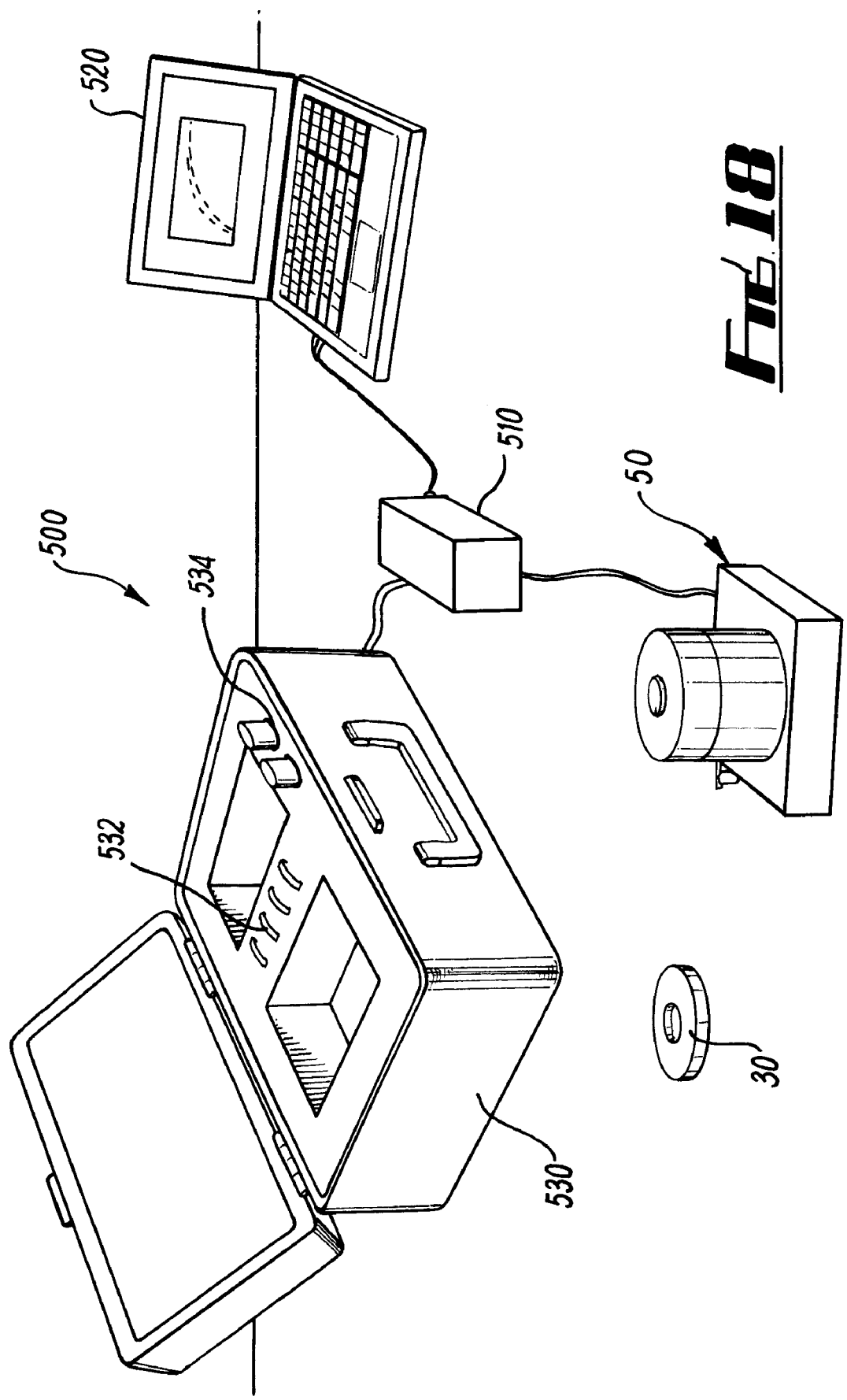
FIG. 18 shows components of a portable system in accordance with an embodiment of the invention.

A preferred embodiment of the invention is configured as a system of portable apparatus, as shown in FIG.18. The system 500 comprises an apparatus 50, an auxiliary unit 510, and a portable computer 520, and a case 530. The auxiliary unit 510 contains a power supply for the apparatus 50, and an interface for data input to and output from the apparatus 50 and the computer 520. The power supply in this example is a mains adaptor, although in other embodiments it may comprise a battery pack to increase portability. A data logger and microcontroller are also included in the auxiliary unit. The case 530 is configured to house the apparatus 50 and the auxiliary unit 510, and comprises receptacles 532, 534 for test pieces 30 and fluid sample containers 536. The portable computer is capable of analysing and displaying data from the auxiliary unit, and may also be used to configure the operation of the system. However, the system may be left to run without being connected to the portable computer 520.

The invention in this aspect allows the apparatus to be taken to a site, such as an offshore location or laboratory, for performance of the methods of the invention. The apparatus may be used to test the swell profile of a test piece in a fluid sample extracted from a wellbore at the drill site. It may be used to demonstrate performance of a particular swellable tool configuration at a client site.

Figure 19:
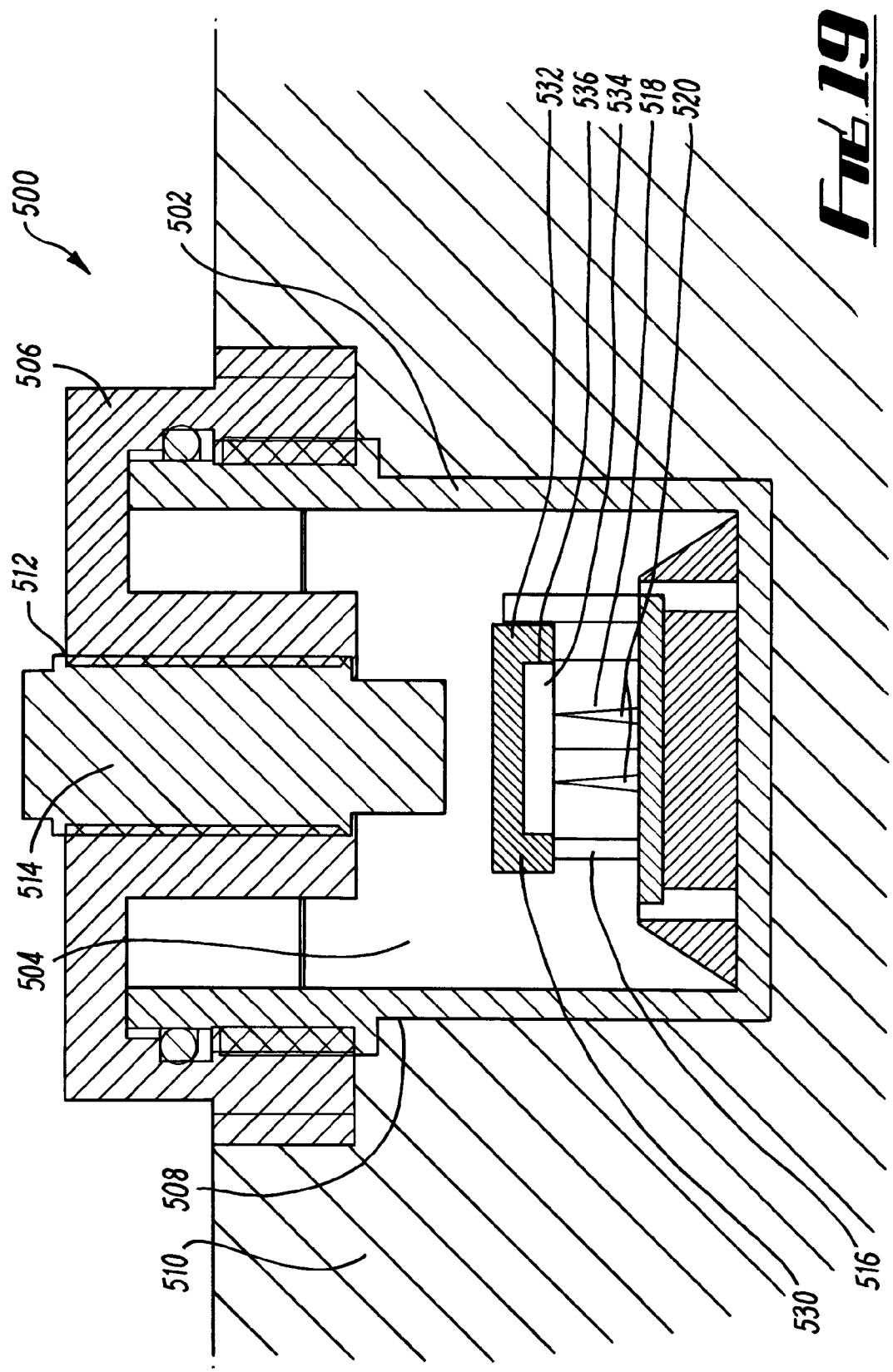
FIG. 19 is a sectional view of the testing apparatus in accordance with an alternative embodiment of the invention.

FIG.19 shows a testing apparatus in accordance with a further alternative embodiment of the invention, which may be used as an alternative or in addition to the testing apparatus of FIG.6, 7 or 9. The apparatus, generally shown at 500, is configured for testing the swell characteristic of a swellable material used in oilfield equipment. The apparatus 500 is similar to and will be understood from the apparatus 50 of FIG.6, although differs in various structural and functional features as will be described below.

The apparatus 500 comprises a substantially cylindrical body comprising a base section 502 and a cap section 506, which together define the internal chamber 504. The base section 502 and the cap section 506 are formed from a suitable metal such as aluminium or an aluminium alloy. The body is shaped and sized to be accommodated in a recess 508 in an aluminium block heater 510. The cap section 506 is fixed to the base section 502 to close the chamber 504. A central aperture 512 in the cap section 506 accommodates an eddy current transducer 514, which extends through the cap section into the fluid chamber 504. The eddy current transducer is for example a Micro-Epsilon group DT3010-A series sensor.

The apparatus 500 comprises a mounting arrangement 516 for a test piece 530. The test piece 530 is similar to test piece 30 and will be understood from FIGS. 4A and 4B and the corresponding description. However, the test piece 530 differs in that the substrate 532, which acts as a carrier and support for the swellable material 534, is formed from aluminium. A recess 536 formed in the face of the disc is filled with a swellable material 534. In this embodiment, the swellable material 534 is not moulded into the recess 536. Rather, the swellable material is a piece of material punched, machined, or cut from a larger body of swellable material. The swellable material 534 is bonded to the substrate 532 on its lower surface and its sides, leaving one exposed surface.

In the previous embodiments, the mounting arrangement 516 included a plate which was moved by the swelling of the test piece, with the position of the plate (or contact pressure in the case of the embodiment of FIG.9) measured by the transducer. However, in this embodiment, the test piece 530 is mounted in an inverted orientation, with the substrate 532 uppermost, and the swellable material 534 lowermost. The test piece 530 is supported on a support member 518, which in this case includes a plurality of needle points 520. The needle points 520 provide a number of point contacts for the test piece, while still allowing fluid circulation and sufficient exposure of the test piece 532 to fluid in the chamber 504.

In use, fluid present in the chamber contacts the swellable material 534 and causes an increase in volume. This increase in volume imparts an upward force on the test piece 532, moving the substrate towards the transducer 514. The transducer measures the displacement of the substrate 532 and the measurement data is recorded.

Omitting a separate plate from the design simplifies the apparatus, reducing its cost and weight and improving its portability. The mounting arrangement 516 is preferable to using of a mesh or porous support for the test piece in some circumstances. For example, water-swellable elastomers such as those including Super-Absorbent Polymers (SAPs)

may exude a residue which has a tendency to block pores in a porous or mesh-like support, reducing fluid access and diminishing the quality of the data. The mounting arrangement 516 offers the advantage that any substance which exudes from the swellable material 534 will pass into the fluid in the chamber 504.

In the foregoing description, the invention is described in the context of testing swellable packers. However, it will be appreciated by one skilled in the art that the principles of the invention may be used wherever swellable components are employed in downhole environments. For example, swellable components are used in a variety of seals, anchors and centralisers. Use of swellable components has also been proposed in downhole actuation mechanisms, valves and flow stemming members. Using the principles of the invention, a relationship may be determined between the swelling of a test piece, and the swelling of a swellable component having a particular configuration. This can then be used to predict the swelling profile of the tool in specific fluids, and may be extended to predict the swelling configuration of components having different dimensions and/or configurations.

The principles and techniques of the invention may also be used in applications to testing of oilfield components and apparatus which are used downhole, and which are not specifically designed to swell. For example, elastomeric materials which are used downhole in a wide range of apparatus, such as o-ring seals and components of downhole pumps, may be selected to avoid or limit the swelling due to fluid exposure where an increase in volume is detrimental to the performance of the apparatus. The invention in its various aspects may therefore be applied to testing and/or predicting the swelling characteristics of components and materials to enable the design and/or specification of oilfield apparatus to mitigate against undesired swelling.

In embodiments described above, the apparatus 50 comprises an eddy current transducer. It may be advantageous to use eddy current transducers with fluids at high temperatures or large variations in temperature. Other transducer types may be used in alternative embodiments. For example non-contacting transducers such as optical, laser and capacitive transducers may be used. In another example, a contacting linear transducer capable of measuring displacement of a piston relative to a body is used. One suitable linear transducer 70 is a contacting linear transducer sold by Positek Limited with product reference number P103. The transducer is in contact with a support plate which moves upwards in the direction of the axis A on swelling of the swellable material, and outputs the displacement measurements as measurement data.

The methods described above make the assumption that the relationships between the swelling characteristics of a test piece and the swelling characteristics of a tool in a given fluid depends on the relative geometry of the tool, and are not dependent on the fluid. However, for a particular tool design, the test can be repeated in a number of different fluids or the same fluid at different activation temperatures. In each case, the test piece measurement data and the tool measurement data are collected from tests carried out in the same format (i.e. the same reference fluids and test temperatures).

If any variations in the swelling profile of test pieces in different fluids are apparent, they can be recorded in the database, for example as separate time-series. When predicting the swelling characteristics in a particular wellbore fluid, data from tests performed with an appropriate fluid (i.e. one with similar composition) can be used. For example, a time-domain scaling multiplier may be selected from a test performed using the closest match of fluid type recorded in the database.

Variations in the swelling profile of test pieces in the same fluid at different temperatures may also be apparent, particularly in the case of water-swelling elastomers and "hybrid" elastomers which swell in aqueous and hydrocarbon fluids. An increase in temperature may increase the maximum swell volume ratio and may also increase the swell rate, reducing the contact time and/or pack-off time. In such circumstances the method may include performing multiple swell-tests at different temperature conditions and deriving a relationship between the swelling characteristics of a test piece and the swelling characteristics of a swellable component which is temperature dependent. One simple method is to calculate time-domain scaling multipliers in the manner described above for multiple different temperature tests and to plot the results against temperature to derive a relationship between the temperature and the multiplier. For given wellbore conditions with a known temperature, an appropriate time scale multiplier may be selected for predicting the performance of a swelling component based on test-piece measurement data.

In another simple example method, the maximum swelling volume may be determined from multiple different temperature tests with the results plotted against temperature to allow derivation of a relationship between the temperature and the maximum swelling volume. This allows determination of swell volume scaling multipliers, which may be applied to the swell volume data to normalise the data for different temperature conditions. For given wellbore conditions with a known temperature, the normalised or rescaled volume data can be used in conjunction with the time-domain scaling multiplier in the manner described above to predict the performance of a swelling component based on test-piece measurement data.

The invention provides a method and apparatus for use in testing the swell characteristics of swellable components used in downhole exploration or production equipment, such as swellable packers. A method of measuring a test piece using a testing apparatus with a fluid chamber and a transducer is described. Measured data can be compared with data measured from a sample section of a tool to determine a relationship between swell characteristics. The determined relationships can then be used to calculate or predict swelling characteristics of swellable components, for example particular packer designs, in specific fluid samples.

Variations to the above-described embodiments of the invention are within the scope of the invention, and the invention extends to combinations of features other than those expressly claimed herein.

What is claimed is:

1. A method of assessing a swellable component for downhole hydrocarbon exploration or production equipment, the method comprising the steps of:
   providing a test piece comprising a swellable material in a fluid chamber of a testing apparatus;
   exposing the test piece to a triggering fluid;
   measuring, using the testing apparatus, a swell characteristic of the test piece to provide a test piece measurement data set;
   providing a swellable component measurement data set corresponding to a swell characteristic of a swellable component; and
   analyzing the test piece measurement data set and the swellable component measurement data set to determine a relationship between the swell characteristic of the test piece and the swell characteristic of the swellable component.

2. The method of claim 1, comprising the additional step of recording the test piece measurement data set in a data storage device.

3. The method of claim 1, wherein the test piece measurement data set comprises a time series of the swell characteristic of the test piece.

4. The method of claim 1, comprising the additional step of generating a report of the swell characteristic of the test piece.

5. The method of claim 1, comprising the additional step of generating a display representative of the swell characteristic from the test piece measurement data set and displaying to a user.

6. The method of claim 1, wherein the test piece measurement data set comprises the measurement of a dimension of the test piece.

7. The method of claim 1, wherein the testing apparatus comprises a non-contact transducer that tracks movement of a target coupled to the test piece.

8. The method of claim 7, wherein the testing apparatus comprises an eddy current transducer.

9. The method of claim 1, wherein the test piece measurement data set comprises a pressure measurement.

10. The method of claim 1, wherein the triggering fluid is a sample of a fluid to which downhole equipment will be exposed in a wellbore operation.

11. The method of claim 1, comprising the additional step of exposing the test piece to a second fluid.

12. The method of claim 1, comprising the additional step of circulating the triggering fluid through the chamber.

13. The method of claim 1, comprising the additional step of changing a temperature of the chamber of the apparatus.

14. The method of claim 13, comprising the additional step of increasing the temperature of the test piece.

15. The method of claim 1, comprising the additional step of determining a relationship between the swell characteristic of the test piece and the swell characteristic of a swellable component of a downhole tool.

16. The method of claim 1, comprising the additional step of calculating swelling data for a proposed swellable component of hydrocarbon exploration or production equipment from the test piece measurement data set using the determined relationship between the swell characteristic of the test piece and the swell characteristic of the swellable component.

17. A method of analysing data in an assessment of a swellable component of downhole hydrocarbon exploration or production equipment, the method comprising the steps of:
providing a first measurement data set comprising measurement data corresponding to a test piece swell characteristic;
providing a second measurement data set comprising measurement data corresponding to a swellable component swell characteristic; and
comparing the first and second measurement data sets to determine a relationship between the test piece swell characteristic and the swellable component swell characteristic.

18. The method of claim 17, wherein the first measurement data set comprises data corresponding to a dimension of the test piece.

19. The method of claim 18, wherein the first measurement data set comprises data corresponding to a thickness of the test piece.

20. The method of claim 17, wherein the second measurement data set comprises data corresponding to a dimension of the swellable component.

21. The method of claim 20, wherein the second measurement data set comprises data corresponding to an outer diameter of the swellable component.

22. The method of claim 17, wherein the second measurement data set comprises data measured from a swellable component sample.

23. The method of claim 17, wherein at least one of the first and second measurement data sets comprises data corresponding to a pressure or force exerted by swelling of the test piece or swellable component respectively.

24. The method of claim 17, wherein the first measurement data set comprises a first time series.

25. The method of claim 17, wherein the second measurement data set comprises a second time series.

26. The method of claim 17, wherein the first measurement data set comprises a first time series and the second measurement data set comprises a second time series.

27. The method of claim 26, comprising the additional step of deriving a time domain scaling multiplier for time values of one of the first or second time series.

28. The method of claim 27, comprising the additional steps of:
setting a value of a time domain scaling multiplier; and
applying the time domain scaling multiplier to time values of one of the first or second time series to generate a scaled time series.

29. The method of claim 28, comprising the additional step of optimising the time domain scaling multiplier to minimise a difference between the scaled time series and the other, unscaled time series.

30. The method of claim 17, comprising the additional step of providing swellable component configuration data, and storing the swellable component configuration data in a database with the determined relationship.

31. The method of claim 30, wherein the swellable configuration data comprises at least one of: dimensions of the swellable component; shape of the swellable component; materials used in the swellable component; and construction techniques used to form the swellable component.

32. The method of claim 30, comprising the additional step of deriving a ratio of a dimension of the swellable component to a dimension of the test piece from the swellable component configuration data.

33. The method of claim 32, comprising the additional step of deriving a ratio of a thickness of a swellable component a thickness of a swellable material in the test piece from the swellable component configuration data.

34. The method of claim 17, comprising the additional steps of:
providing an additional measurement data set comprising measurement data corresponding to an additional swellable component swell characteristic; and
comparing the first and additional measurement data sets to determine an additional relationship between a test piece swell characteristic and the additional swellable component swell characteristic.

35. The method of claim 34, further comprising repeating the providing and comparing steps for at least one further swellable component and storing the plurality of determined relationships in a database with swellable component configuration data.

36. The method of claim 35, comprising the additional step of deriving a further relationship between the swellable component configuration data and the plurality of determined relationships.

37. The method of claim 36, comprising the additional step of deriving a further relationship between the ratio of a thickness of a swellable component to a thickness of a swellable material in the test piece and a time domain scaling multiplier.

38. A method of calculating swelling data for a swellable component of downhole hydrocarbon exploration or production equipment, the method comprising the steps of:
providing a test piece measurement data set, wherein the test piece measurement data set is obtained by: disposing a test piece comprising a swellable material in a fluid chamber of a testing apparatus, exposing the test piece to a fluid, and measuring a test piece swell characteristic; and
calculating swelling data for the swellable component from the test piece measurement data set by using a known relationship between the test piece swell characteristic and a swell characteristic of the swellable component.

39. The method of claim 38, comprising the additional step of obtaining the test piece measurement data set by performing a test on the test piece.

40. The method of claim 39, comprising the additional step of simulating a wellbore operation by altering one or more of: the fluid composition, the fluid volume, the fluid temperature, or the test piece temperature during the test.

41. The method of claim 38, wherein the fluid is selected to correspond to a fluid to which the swellable component will be exposed during a downhole operation.

42. The method of claim 38, wherein the fluid is a sample of wellbore fluid to which the swellable component will be exposed during a wellbore operation.

43. The method of claim 38, wherein the swelling data comprises a time series of swelling characteristics of the swellable component.

44. The method of claim 38, comprising the additional step of assessing the suitability of the swellable component for a downhole operation based on the calculated swelling data.

45. The method of claim 38, comprising the additional step of calculating swelling data for a plurality of different swellable components using relationships between a test piece swell characteristic and swell characteristics of the respective swellable component.

46. The method of claim 38, wherein the swellable component is a part of a wellbore packer.

47. The method of claim 46, comprising the additional step of calculating a time at which the wellbore packer will contact a borehole wall of known dimensions.

48. The method of claim 46, comprising the additional step of calculating the additional step of a time at which the wellbore packer will exert its maximum pressure against a borehole wall.

49. The method of claim 46, comprising the additional step of calculating a pressure differential rating for the wellbore packer in a borehole of known dimensions.

50. A method of assessing the suitability of a swellable component of a downhole tool for a wellbore operation, the method comprising:
providing a database comprising swellable component configuration data and one or more relationships associated with the swellable component configuration data, wherein the one or more relationships are relationships between a swell characteristic of a swellable component configured according to the swellable component configuration data and a swell characteristic of a test piece;
providing a test piece measurement data set;
calculating swelling data for a proposed swellable component configuration from the test piece measurement data set, using a relationship accessed from the database; and
assessing the suitability of the swellable component configuration for use in the downhole tool based on the calculated swelling data.

51. The method of claim 50 wherein the swellable configuration data is at least one of data selected from a group consisting of: a dimension of the swellable component, a shape of the swellable component, a material used in the swellable component, and a construction technique used to form the swellable component.

52. The method of claim 50 wherein the database comprises swellable component configuration data relating to a plurality of swellable component configurations and a plurality of associated relationships.

53. The method of claim 50 comprising generating a report from the calculated swelling data.

54. The method of claim 50 comprising generating a display representative of the swell characteristic from the calculated swelling data and displaying to a user.

55. The method of claim 50 further comprising:
obtaining the test piece measurement data set by performing a test on the test piece, the test comprising disposing the test piece comprising a swellable material in a fluid chamber of a testing apparatus;
exposing the test piece to a fluid; and
measuring a swell characteristic of the test piece.

56. The method of claim 55 further comprising simulating a wellbore operation by altering one or more of the fluid composition, the fluid volume, the fluid temperature, or the test piece temperature during the test.

57. The method of claim 55 wherein the fluid is selected to correspond to a fluid to which the swellable component will be exposed during a wellbore operation.

58. The method of claim 55 wherein the fluid is a sample of wellbore fluid to which the swellable component will be exposed during a wellbore operation.

59. The method of claim 50 comprising calculating swelling data for a plurality of different swellable components using relationships between a swell characteristic of a test piece and the respective swell characteristics of the swellable components.

60. The method of claim 50 wherein the swellable component is a part of a wellbore packer.

61. The method of claim 60 further comprising:
calculating a time at which the wellbore packer will contact a borehole wall of known dimensions; and
comparing the calculated time with a desired wellbore packer contact time to assess the suitability of the swellable component configuration for the wellbore packer.

62. The method of claim 60 further comprising:
calculating a time at which the wellbore packer will exert its maximum pressure against a borehole wall; and
comparing the calculated time with a desired pack-off time to assess the suitability of the swellable component configuration for the wellbore packer.

63. The method of claim 60 further comprising:
calculating a pressure differential rating for the wellbore packer in a borehole of known dimensions; and
comparing the calculated pressure differential rating with a desired pressure differential rating to assess the suitability of the swellable component configuration for the wellbore packer.

64. A method of selecting a swellable component configuration for a downhole tool, the method comprising:
providing a database comprising swellable component configuration data and one or more relationships associated with the swellable component configuration data, wherein the one or more relationships are relationships between a swell characteristic of a swellable component configured according to the swellable component configuration data and a swell characteristic of a test piece;

providing a test piece measurement data set;

providing input data comprising desired swell parameters of a downhole tool;

calculating swelling data for a plurality of swellable component configuration data from the test piece measurement data set, using one or more relationships accessed from the database; and selecting one or more swellable component configurations for the downhole tool according to the input data and the calculated swelling data.

65. The method of claim 64 further comprising constructing the downhole tool according the selected one or more swellable component configurations.

66. The method of claim 64 wherein the swellable configuration data is at least one of data selected from a group consisting of: a dimension of the swellable component; a shape of the swellable component; a material used in the swellable component; and a construction technique used to form the swellable component.

67. The method of claim 64 wherein the database comprises swellable component configuration data relating to a plurality of swellable component configurations, and a plurality of associated relationships.

68. The method as claimed in claim 64 further comprising generating a report from the calculated swelling data.

69. The method as claimed in claim 64 further comprising
generating a display representative of the swell characteristic from the calculated swelling data; and
displaying the display.

70. The method of claim 64 comprising obtaining the test piece measurement data set by performing a test on the test piece, the test comprising disposing the test piece comprising a swellable material in a fluid chamber of a testing apparatus, exposing the test piece to a fluid, and measuring a swell characteristic of the test piece.

71. The method of claim 70 comprising simulating a wellbore operation by altering one or more of the fluid composition, the fluid volume, the fluid temperature, or the test piece temperature during the test.

72. The method of claim 70 wherein the fluid is selected to correspond to a fluid to which the swellable component will be exposed during a wellbore operation.

73. The method of claim 70 wherein the fluid is a sample of wellbore fluid to which the swellable component will be exposed during a wellbore operation.

74. The method of claim 70 wherein the swellable component is a part of a wellbore packer.

75. The method of claim 74 further comprising:
calculating a plurality of times at which the wellbore packer will contact a borehole wall of known dimensions for a plurality of swellable component configuration data; and
comparing the calculated times with a desired wellbore packer contact time to select the swellable component configuration for the wellbore packer.

76. The method of claim 74 comprising:
calculating a plurality of times at which the wellbore packer will exert its maximum pressure against a borehole wall for a plurality of swellable component configuration data; and
comparing the calculated times with a desired pack-off time to select the swellable component configuration for the wellbore packer.

77. The method of claim 74 further comprising:
calculating a plurality of pressure differential ratings for the wellbore packer in a borehole of known dimensions for a plurality of swellable component configuration data; and
comparing the plurality of calculated pressure differential ratings with a desired pressure differential rating to select the swellable component configuration for the wellbore packer.

* * * * *